United States Patent
Malackowski et al.

(10) Patent No.: US 8,535,342 B2
(45) Date of Patent: Sep. 17, 2013

(54) POWERED SURGICAL HANDPIECE WITH AN ANTENNA FOR READING DATA FROM A MEMORY INTEGRAL WITH A CUTTING ACCESSORY ATTACHED TO THE HANDPIECE

(75) Inventors: Don Malackowski, Schoolcraft, MI (US); Wenjie Deng, San Jose, CA (US); José Luis Moctezuma de la Barrera, Freiburg (DE); James Keith Rains, Kalamazoo, MI (US); Mark Wasserman, Delton, MI (US)

(73) Assignee: Stryker Corporation, Kalamazoo, MI (US)

( * ) Notice: Subject to any disclaimer, the term of this patent is extended or adjusted under 35 U.S.C. 154(b) by 245 days.

(21) Appl. No.: 12/493,826

(22) Filed: Jun. 29, 2009

(65) Prior Publication Data

US 2009/0292304 A1 Nov. 26, 2009

Related U.S. Application Data

(62) Division of application No. 10/214,937, filed on Aug. 8, 2002, now abandoned.

(60) Provisional application No. 60/310,957, filed on Aug. 8, 2001.

(51) Int. Cl.
*A61B 17/32* (2006.01)

(52) U.S. Cl.
USPC ........................................................ 606/170

(58) Field of Classification Search
USPC ............ 606/167, 170–173, 79–82; 340/10.5; 361/749–751
See application file for complete search history.

(56) References Cited

U.S. PATENT DOCUMENTS

| | | | |
|---|---|---|---|
| 4,090,802 A | 5/1978 | Bilz | |
| 4,355,977 A | 10/1982 | Ota et al. | |
| 4,425,060 A | 1/1984 | Bilz et al. | |
| 4,588,335 A | 5/1986 | Pearson, Jr. | |
| 4,605,348 A | 8/1986 | DeCaro | |
| 4,705,038 A | 11/1987 | Sjostrom et al. | |
| 4,887,929 A | 12/1989 | Hale | |
| 5,176,143 A | 1/1993 | Eckerle et al. | |
| 5,180,363 A * | 1/1993 | Idemoto et al. ................. 604/22 |

(Continued)

FOREIGN PATENT DOCUMENTS

| | | |
|---|---|---|
| DE | 3046485 A1 | 7/1982 |
| DE | 3917876 A1 | 12/1990 |

(Continued)

OTHER PUBLICATIONS

U.S. Appl. No. 10/210,325, filed Aug. 1, 2002.

(Continued)

*Primary Examiner* — Elizabeth Houston

(57) ABSTRACT

A powered surgical handpiece that includes a motor for actuating a cutting accessory. The handpiece has a housing with a bore for receiving the cutting accessory and a coupling member internal to the bore that releasably engages and actuates the cutting accessory. A coil is mounted to the housing adjacent the bore. More particularly, the coil is located so that when the cutting accessory is seated in the bore, the coil is able to exchange signals with a complementary coil integral with the cutting accessory. A locking assembly mounted to the housing releasably holds the cutting accessory in the bore.

20 Claims, 25 Drawing Sheets

(56) References Cited

U.S. PATENT DOCUMENTS

| | | | |
|---|---|---|---|
| 5,192,292 | A | 3/1993 | Cezena et al. |
| 5,248,229 | A | 9/1993 | Bilz |
| RE34,556 | E | 3/1994 | Sjostrom et al. |
| 5,383,874 | A | 1/1995 | Jackson et al. |
| 5,400,267 | A | 3/1995 | Denen et al. |
| 5,443,082 | A | 8/1995 | Mewburn |
| 5,460,490 | A | 10/1995 | Carr et al. |
| 5,628,731 | A | 5/1997 | Dodge et al. |
| 5,632,759 | A | 5/1997 | Rexroth |
| 5,747,953 | A | 5/1998 | Philipp |
| 5,810,770 | A | 9/1998 | Chin et al. |
| 5,822,652 | A * | 10/1998 | Elhatem et al. ............... 399/90 |
| 6,017,354 | A * | 1/2000 | Culp et al. .................. 606/170 |
| 6,019,745 | A | 2/2000 | Gray |
| 6,092,722 | A | 7/2000 | Heinrichs et al. |
| 6,126,670 | A | 10/2000 | Walker et al. |
| 6,223,633 | B1 | 5/2001 | Chien-Chich |
| 6,312,441 | B1 | 11/2001 | Deng |
| 6,315,060 | B1 | 11/2001 | Schuda et al. |
| 6,604,744 | B2 | 8/2003 | Monge |
| 6,626,862 | B1 | 9/2003 | Duchon et al. |
| 6,688,611 | B2 | 2/2004 | Gifford et al. |
| 6,960,894 | B2 | 11/2005 | Carusillo et al. |
| 7,086,111 | B2 | 8/2006 | Hilscher et al. |
| 2003/0093103 | A1 | 5/2003 | Malackowski et al. |
| 2004/0010258 | A1 | 1/2004 | Carusillo et al. |
| 2004/0059363 | A1 | 3/2004 | Alzarez et al. |
| 2004/0092991 | A1 | 5/2004 | Deng |

FOREIGN PATENT DOCUMENTS

| | | |
|---|---|---|
| EP | 0630820 A1 | 12/1994 |
| EP | 0951921 A2 | 10/1999 |
| EP | 1110504 A2 | 6/2001 |
| JP | 07178107 A | 7/1995 |
| NL | 1001018 C2 | 2/1997 |
| WO | WO 9410921 A1 | 5/1994 |
| WO | WO 0024318 A1 | 5/2000 |

OTHER PUBLICATIONS

U.S. Appl. No. 60/395,881, filed Jul. 15, 2002.
PCT/US2002/025127 International Search Report, Mar. 2003.
PCT/US2002/025127 Partial European Patent Office Search Report, Nov. 27, 2002.

* cited by examiner

POWERED SURGICAL HANDPIECE WITH AN ANTENNA FOR READING DATA FROM A MEMORY INTEGRAL WITH A CUTTING ACCESSORY ATTACHED TO THE HANDPIECE

RELATIONSHIP TO EARLIER FILED APPLICATION

This Application is a divisional of application Ser. No. 10/214,937, filed 8 Aug. 2002, now abandoned which claims priority from the Applicant's U.S. Patent Application Ser. No. 60/310,957, SURGICAL TOOL SYSTEM WITH A CUTTING ACCESSORY THAT CONTAINS A MEMORY WITH DATA THAT DESCRIBES THE OPERATING CHARACTERISTICS OF THE CUTTING ACCESSORY, filed 8 Aug. 2001. The contents of the priority applications are incorporated herein by reference.

BACKGROUND OF THE INVENTION

The Applicant's Assignee's U.S. Pat. No. 6,017,354, entitled INTEGRATED SYSTEM FOR POWERED SURGICAL TOOLS, issued Jan. 25, 2000, and incorporated herein by reference, describes a surgical tool system with a handpiece that is removably attached to a control console. Internal to the handpiece is a memory, a NOVRAM. The NOVRAM contains data that describes the operating characteristics of the handpiece. For example, if the handpiece includes a motor, its NOVRAM includes data indicating the maximum speed at which the motor should run and, for given speeds, the maximum torque the motor is allowed to develop. Each time a new handpiece is attached to the control console, the data in the handpiece NOVRAM is read by a complementary processor in the control console. The control console, based on the handpiece NOVRAM data, then supplies the appropriate energizaton signal to the handpiece motor.

An advantage of the foregoing system is that it allows a single control console to be used to supply the energizaton signals that are applied to the handpiece that have different power consuming units, such as motors. Thus, a single control console can be used to operate a first handpiece with a motor that rotates at speeds under 3,000 RPM and requires 350 Watts or more of power, a second handpiece that has a motor that operates at speeds over 70,000 RPM and that requires approximately 150 Watts of power and a third handpiece that operates at speeds between 10,000 to 40,000 RPM and that requires only 40 Watts of power.

In most surgical systems, the handpiece is not the actual component that is applied to the surgical site in order to accomplish a surgical task. These components are, what are referred to as cutting accessories.

Typically, a single handpiece is used to actuate a number of different types of cutting accessories. For example, a handpiece designed to perform some forms of ear, nose and throat surgery is designed to actuate both burrs and cutters. Burrs are cutting accessories designed to selectively shape and remove hard tissue, bone. Cutters are cutting accessories that are employed to selectively shape and remove soft tissue such as sinus membrane tissue.

While a single handpiece is designed to actuate different types of cutting accessories, the accessories themselves often have different operating characteristics. For example, some burrs may have a preferred operating speed of 6,000 RPM and may be designed to operate at speeds of up to 10,000 RPM. In contrast, some cutters may have a preferred operating speed of 2,000 RPM and may be designed to operate at a maximum speed of 5,000 RPM. Moreover, some cutting accessories are operated in a different manner than other cutting accessories. For example, a burr is driven, rotated, in a single direction. A cutter is typically oscillated. In other words, when a cutter is actuated, it is typically rotated through an arc of X degrees in a first direction and then rotated in the opposite direction through the same arc. Once this first rotation cycle is complete, the motor driving the cutter repeats this rotational pattern.

Often, during the course of a single surgical procedure, the surgeon will want to apply two or more different cutting accessories to the surgical site in order to accomplish the procedure. Typically, the surgeon will use a single handpiece to actuate these different cutting accessories. Each time the surgeon attaches a different type of cutting accessory to the handpiece, it may be necessary for the surgeon or other operating room personnel to reconfigure the surgical system used to drive the cutting accessory to set it for the specific characteristics of that accessory. When surgical personnel have to do this during the course of a surgical procedure, it can increase the overall time it takes for the procedure to be performed. This is contrary to one of the goals of modern surgery which is that it is desirable to perform a surgical procedure as quickly as possible in order to hold the overall time a patient is kept under anesthesia to a minimum.

Moreover, having to have an individual in the operating room set the surgical system to the operating characteristics of the cutting accessory that the system is being used to operate introduces the possibility that, due to human error, these characteristics will be improperly entered.

There have been some efforts at providing cutting accessories with type-identifying indicators, typically magnets. The handpieces to which these accessories are attached are provided with sensors. These sensors detect the presence/absence of the magnets and generate signals representative of what was sensed back to the control console. The processor in the control console, based on the signals from the handpiece sensors, then configures the system.

The above system, while of some utility, only provides a limited amount of data about the cutting accessory attached to the system handpiece. This is because, due to space considerations, only a limited number of indicators can be mounted to a cutting accessory and only a limited number of sensors can be fitted in the head end of the handpiece designed to actuate the accessory. For example, known commercial systems of this design have handpieces with two sensors. Each sensor is designed to detect the presence/absence of a separate cutting accessory-mounted magnet. Thus, these systems simply provide 2 bits of data. Even if it were possible for the number of magnets in the cutting accessories and the number of complementary handpiece sensors to be doubled, the resultant system would only be able to provide 4 bits of accessory specific data.

Thus, in the current systems, the indicators mounted to a cutting accessory are only employed to provide data that describes a basic operating characteristic of the accessory or that describes its type. For example, the indicator may be employed to describe basic speed and torque ranges of the cutting accessory or, for example, that the accessory is a burr. Regardless of the specific nature of this data, the control console processor, uses the data to reference complementary control data in a look-up table or other circuitry internal to the control console. The actual regulation of the handpiece is controlled by reference to this previously stored characteristic-data.

Thus, in the foregoing cutting accessory recognition system, the actual control of the handpiece is based on operating parameters that have been previously loaded into the control console. If a new accessory is provided that has operating characteristics different than those that have been loaded into the control console, the console will not automatically configure itself to operate the handpiece in accordance with those parameters. In order for this control to be accomplished, the control console has to be loaded with the new operating characteristic data. Moreover, given the limited amount of data that can be read from the indicators of the current systems, these data may be insufficient to provide all the information a control console could use to regulate its operation based on the characteristics of the attached cutting accessory.

DETAILED DESCRIPTION

Figure 1:
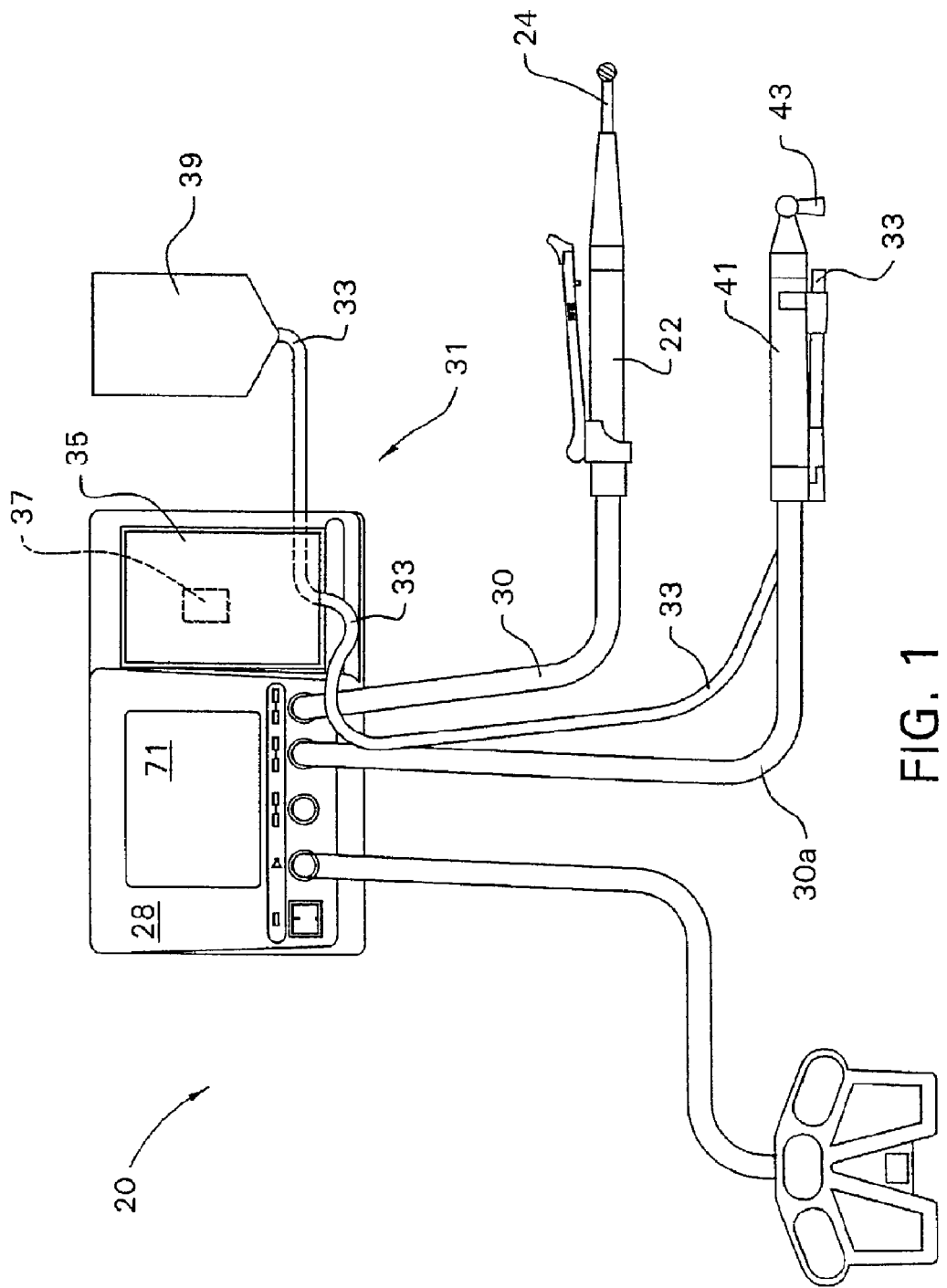
FIG. 1 depicts the basic system of this invention.

FIG. 1 depicts the surgical system 20 of this invention. System 20 includes a surgical handpiece 22 that is used to actuate a cutting accessory 24 that is removably attached to the handpiece. Internal to the handpiece is a motor 26 (FIG. 2) that is actuated to drive the cutting accessory 24. The handpiece 22 is removably attached to a control console 28 by a flexible cable 30. The control console 28 contains circuitry that is used to supply energization signals to the handpiece motor 26. The regulation of these energization signals is controlled by a microprocessor, controller 70 (FIG. 3), internal to the control console 28. Internal to the handpiece 22 or the cable 30 is a NOVRAM 32. (When the NOVRAM 32 is in the cable 30, the cable is integrally attached to the handpiece 22.) The NOVRAM 32 contains data that describes the operating characteristics of the handpiece 22. These data include: information that identifies the type of handpiece; information that describes the operating characteristics of the handpiece motor; the identification of the type of output signals provided by any sensors internal to the handpiece; and information useful for correcting the signals produced by the handpiece sensors to correct for their individual calibration characteristics. More information on the types of data contained in the handpiece NOVRAM 32 and how this information is used to regulate the operation of the handpiece 22 by the system 20 is found in U.S. Pat. No. 6,017,354, which is, again, incorporated herein by reference.

FIG. 1 further includes disposable tubing set 31. The tubing set 31 includes tubing 33 and a cartridge 35. A portion of the tubing 33 extends through and is secured to the cartridge 35. The cartridge includes an identification chip 37.

A first end of the tubing 33 is secured to and receives irrigation fluid, such as saline from an IV bag 39. The cartridge 35 is mounted onto the control console 28. A positive displacement pump (not shown) of the control console pumps the solution to a second distal end of the tubing 33 to irrigate a surgical site. The tubing 33 is adjacent an irrigation/cutting handpiece 41. A flexible cable 30a connects the handpiece 41 to the control console 28. The tubing 33 is positioned adjacent to the entire length of the cable 30a. A cutting saw 43 is located at a distal end of the handpiece 41. Other cutting elements can be utilized in place of the saw 43.

The cartridge 35 can be any structure designed for securement to the control console. In some embodiments, the tubing set 31 comprises only tubing 31 and an identification chip 37. In this instance, the tubing 33 is secured to the control console 28 so that the pump can pump irrigation fluid to the distal end of the tubing.

In operation, the user of the irrigation/cutting handpiece 41 actuates the cutting saw 43. Power is supplied to the cutting saw via cable 30a. When the cutting saw 43 is actuated, tubing 33 provides irrigation fluid to the surgical site.

When the cartridge 35 is installed onto the console 28, a coil (not shown) mounted on the console adjacent the cartridge reads data from the identification chip 37. The data provides the diameter, size and any other relevant properties for the tubing 33. The control console 28 then controls the positive displacement pump to provide a proper flow rate for the irrigation fluid being applied to the surgical site during cutting. Thus, a user need not manually set specific control values for the pump.

Since the tubing set 31 is disposable, typically only data is read from the identification chip 37. However, in some embodiments data is sent to the chip 37 indicating that the tubing set has been used and must be disposed of.

In some embodiments, no cartridge 35 is present. The tubing 33 is wrapped or otherwise configured to the pump, which is preferably mounted onto the control console 28. In this instance the identification chip 37 is mounted directly to the tubing 33, which comprises of itself, the tubing set 31. However, the identification chip 37 must be positioned adjacent a detector coil connected to the control console 28.

Figure 2:
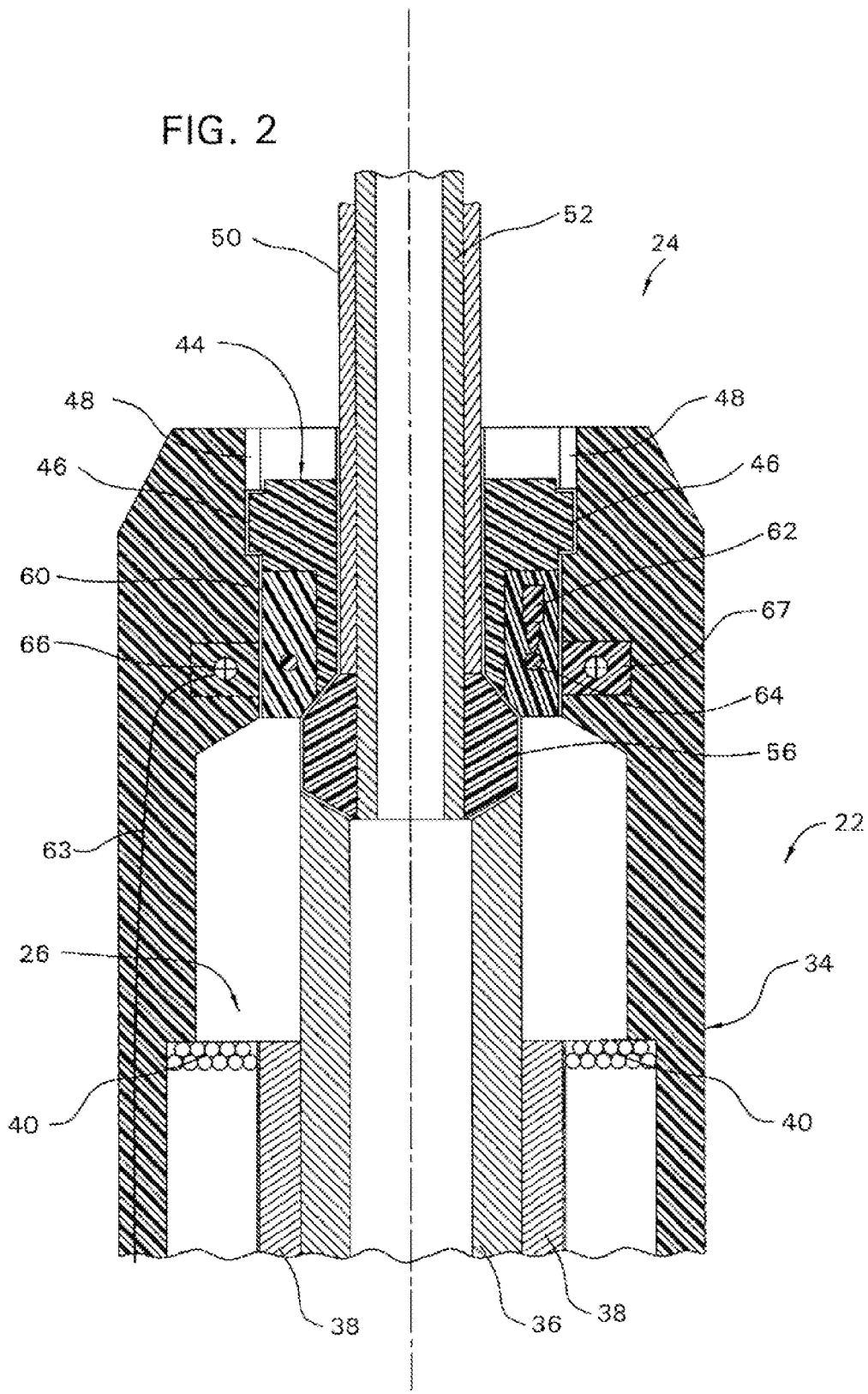
FIG. 2 is a cross-sectional diagram of a cutting accessory seated in the distal end of a handpiece of this invention.

FIG. 2 illustrates the distal end of the handpiece 22 and the proximal end of the cutting accessory 24 of this invention. (In this application, "distal" is used to refer to a portion of a component located away from a surgeon/towards a surgical site; "proximal" refers to a portion of a component located towards the surgeon/away from the surgical site.)

The handpiece 22 has a housing 34. Motor 26 is disposed in the housing 34. The motor 26 has a rotated-sleeve shaped shaft 36 to which a number of magnets 38 are attached. Motor 26 also includes a set of windings 40 that are secured to the inner wall of housing 34 that surround magnets 38. The distal end of housing 34 is open and dimensioned to receive the proximal end of cutting accessory 24.

The cutting accessory 24 includes an outer hub 44 formed of plastic. Outer hub 44 is formed with tabs 46. Tabs 46 seat in complementary notches 48 formed in handpiece housing 34 so as to hold the hub in one place in the housing. A locking mechanism integral with the handpiece, (not illustrated) has members designed to engage the outer hub 44 so as to releasably secure the cutting accessory to the handpiece. For example, some handpieces are provided with a set of ball bearings that are releasably pressed against an opposed outer surface of the outer hub. The Applicant's Assignee's U.S. Pat. No. 6,312,441, POWERED SURGICAL HANDPIECE FOR PERFORMING ENDOSCOPIC PROCEDURES, issued Nov. 6, 2001 and incorporated herein by reference discloses how one such locking assembly works. Alternatively, spring arms may be releaseably held against the outer hub. The Applicant's Assignee's U.S. Pat. No. 5,192,292, SURGICAL APPARATUS FOR ARTHROSCOPIC SURGERY, issued Mar. 9, 1993 and incorporated herein by reference discloses one version of this type of locking assembly. Thus, the actual type of handpiece locking assembly that holds the cutting accessory to the 24 to the handpiece 22 and complementary outer hub geometry may vary.

An outer tube 50 extends distally forward from the outer hub 44 away from the handpiece 22. The cutting accessory 24 also includes an inner tube 52 that is disposed inside the outer tube 50. The distal head end of the inner tube 52, (end not illustrated) is provided with some type of cutting member to selectively shape and/or remove the tissue to which it is applied. The inner tube 52 extends through both the outer tube 52 and the outer hub 44. The proximal end of the inner tube is attached to an inner hub 56, sometimes referred to as a drive coupling, that is located against the proximal facing face of the outer hub 44.

When the cutting accessory 24 is fitted in the handpiece, inner hub 56 is located inside a cavity located in the distal end of the handpiece housing 34. The proximal end of the inner tube 52 and inner hub 56 is seated over the open distal end of handpiece shaft 36. Complementary teeth on the shaft 36 and the inner hub 56 releasably hold the inner hub to the shaft so that the inner hub will rotate in unison with the shaft 36 (teeth not illustrated).

An identification sleeve 60 is fitted over the outer hub 44. Sleeve 60 is formed of plastic and may provide some of the structural strength of the outer hub 44. Internal to sleeve 60 is a small semiconductor that functions as an identification chip 62. Also disposed inside sleeve 60 is a coil 64. In the depicted version of the invention, coil 64 extends annularly around sleeve 60. The ends of coil 64 are, as described below, connected to components internal to identification chip 62.

The distal end, the head end, of handpiece housing 34 is provided with a separate annular coil 66. The opposed ends of coil 66 are connected by conductors 63 (one shown) and cable 30 to circuitry internal to the control console 28. Collectively, the handpiece 22 and cutting accessory 24 are shaped so that coils 64 and 66 are in such proximity to each other that they will collectively inductively transfer signals from/to the circuit internal to the control console to/from the circuit internal to the identification chip 62. Typically, the handpiece housing 34 is formed of metal. Accordingly, in the illustrated versions of the invention, coil 66 is disposed in a ring 67 formed from a plastic that can be subjected to medical sterilization wherein the handpiece is autoclaved at 270.degree. F., subjected to saturated water vapor at 30 psi. One suitable plastic from which ring 67 may be formed is a polyetherimide and glass filed plastic sold by the General Electric Company under the trademark ULTEM. Ring 67 is fitted in a notch, not identified, formed in an interior wall of handpiece housing 34. The inner surface of ring 67 thus defines part of the cavity in which the proximal end of the cutting accessory 24 is seated. The fitting of handpiece coil 66 in ring 67 facilitates the inductive signal transfer between the handpiece coil and the coil 64 integral with the cutting accessory.

Figure 3:
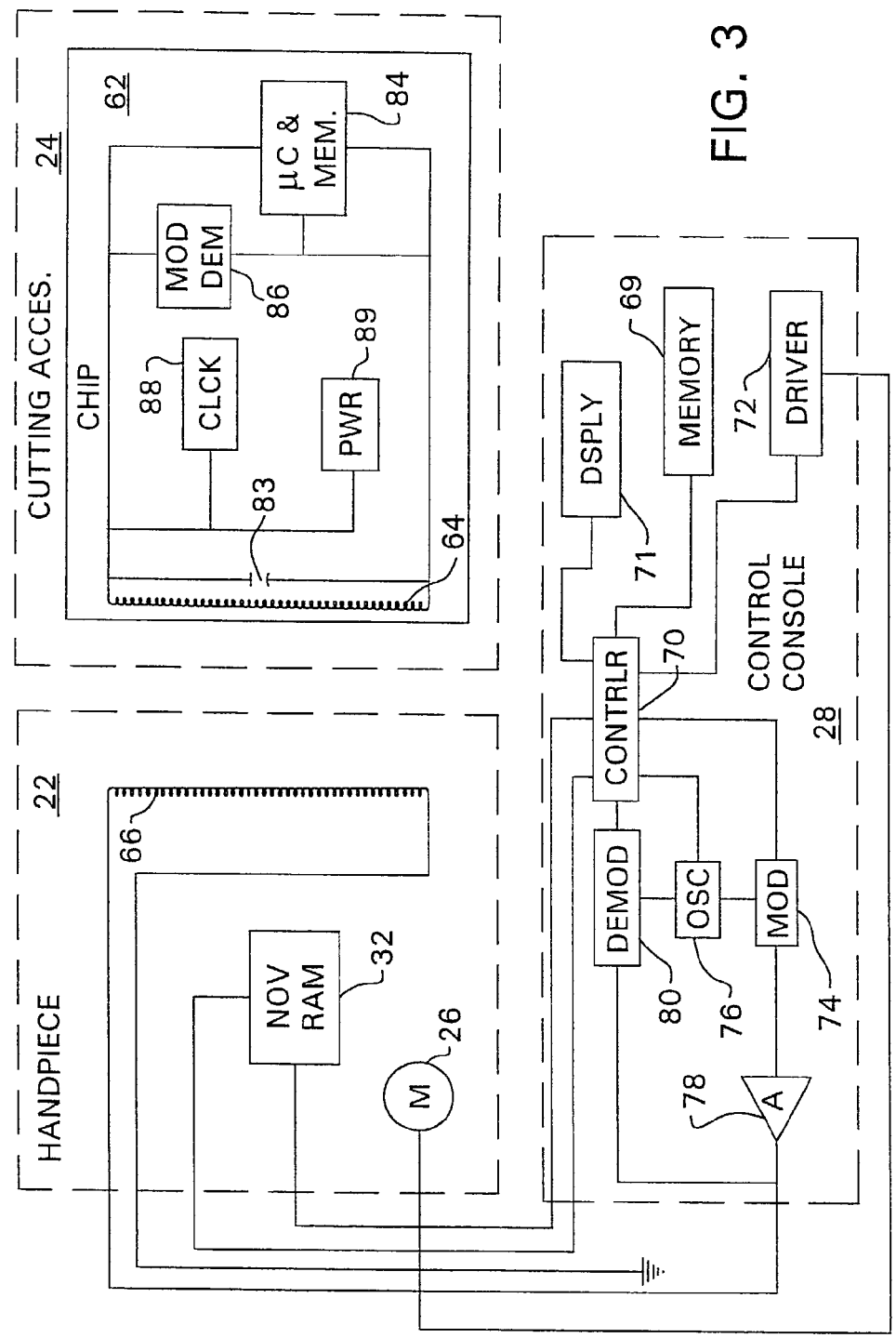
FIG. 3 is a block diagram of the circuitry internal to the control console, the handpiece, and the cutting accessory that is used to store and read data from the accessory that describes the characteristics of the cutting accessory.

FIG. 3 depicts, in block diagram, electrical components internal to control console 28 of system 20 of this invention. The control console 28 includes a controller (CNTRLR) 70 that controls the overall operation of the system 20. Memories, represented by a single memory 69, are also contained in the control console. These memories contain the permanent operating instructions that are executed by controller 70 to control the system and regulate the actuation of the handpiece 22 and the cutting accessory 24. The memories also temporarily store the data that is read from the handpiece NOVRAM 32. As part of its control of system 20, controller 70 generates energization control signals to a driver 72. The driver 72, based in part on the energization control signals, generates energization signals that are applied to the handpiece motor 26. Controller 70 is connected to the handpiece NOVRAM 32 to receive from the NOVRAM the data that describes the operating characteristics of the motor. The control console 28 also includes a touch screen display 71. Controller 70 causes information regarding the state of the system 20 to be presented on the display 71. Controller 70 also causes images of buttons to be presented on the display 71. Operating room personnel regulate the operation of the system 20 by selectively depressing these buttons.

Control console 28 is also connected to a modulator (MOD) 74. Modulator 74 modulates digital signals output by controller 70 so they can be inductively transferred to cutting accessory identification chip 62. In one preferred version of the invention, modulator 74 receives a fixed-frequency signal from an oscillator 76 internal to the control console 28. In one version of the invention, the signal produced by the oscillator 76 is at a frequency of 125 Khz. In another preferred version of the invention, the carrier signal produced by oscillator 76 is at 13.56 MHz.

Modulator 74, based on the bit stream produced by the controller 70, engages in selective amplitude shift keying (ASK) of the carrier signal. In one form of amplitude shift keying, based on the 1's and 0's pattern that forms the bit stream, the modulator 74 selectively transmits/stops transmitting the carrier signal so as to produce a set of variable length rectangular pulses. The amplitude shift keyed signal generated by modulator 74 is amplified by an amplifier 78 internal to the control console 28. The output signal from amplifier 78 is applied to one end of handpiece coil 66.

The end of handpiece coil 66 opposite the end to which amplifier 78 is connected is tied to a demodulator (DEMOD) 80 internal to the control console. Demodulator 80 receives the signal that is coupled to handpiece coil 66, demodulates the signal, and applies the output bit stream to controller 70. A typical demodulator may include a product detector to which the carrier signal is applied from oscillator 76. The output from the detector, which is a multiplication of the signal from the oscillator 76 and the coil 66, is applied to a low-pass filter, also part of the demodulator 80. The output signal from the low pass filter is a bit stream that is applied to the controller 70.

In FIG. 3 oscillator 76 is also shown as connected to controller 70. This is because the signal produced by the oscillator is also used to regulate the writing out of the bit stream that is applied to the modulator 74 and the reading in of the bit stream generated by the demodulator 80.

The identification chip 62 includes a small controller and an electronically programmable memory (μC & MEM) 84. Controller/memory 84 is capable of storing approximately 1 k bits of data. The controller integral with controller/memory 84 is capable of controlling the writing of data into its complementary memory section and the writing out of the contents of the memory. There is also a modulator/demodulator (MOD DEM) 86 fabricated integrally into chip 62. Modulator/demodulator 86 contains the components necessary to demodulate the ASK signal coupled to coil 64 and apply the resultant bit stream to controller/memory 84. Modulator/demodulator 86 also accepts the bit stream output from the controller/memory 84 and produces an ASK modulated signal based on this bit stream. A clock 88 fabricated into chip 62 produces a clock signal that the modulator/demodulator 86 uses as a basis for producing a carrier signal produced an ASK modulated signal.

A capacitor 83 is also fabricated integrally with chip 62. More particularly, chip 62 is designed so that coil 64 is connected across the opposed ends of capacitor 83. When a signal is applied to chip 62 through coil 64, the energy in the high portion of the signal is stored in capacitor 83. This energy is applied directly to a power regulator 89 to function as an energization signal. The power regulator 89 supplies this energization signal to the other sub-circuits internal to the chip 62. (Connections between power regulator 89 and other components of chip 62 not shown.)

In FIG. 3, coil 64 is shown as being integrally part of chip 62. This is one option for the invention. However, as discussed above, it is anticipated that in many versions of the invention, chip 62 and coil 64 will be separate components.

Figure 4:
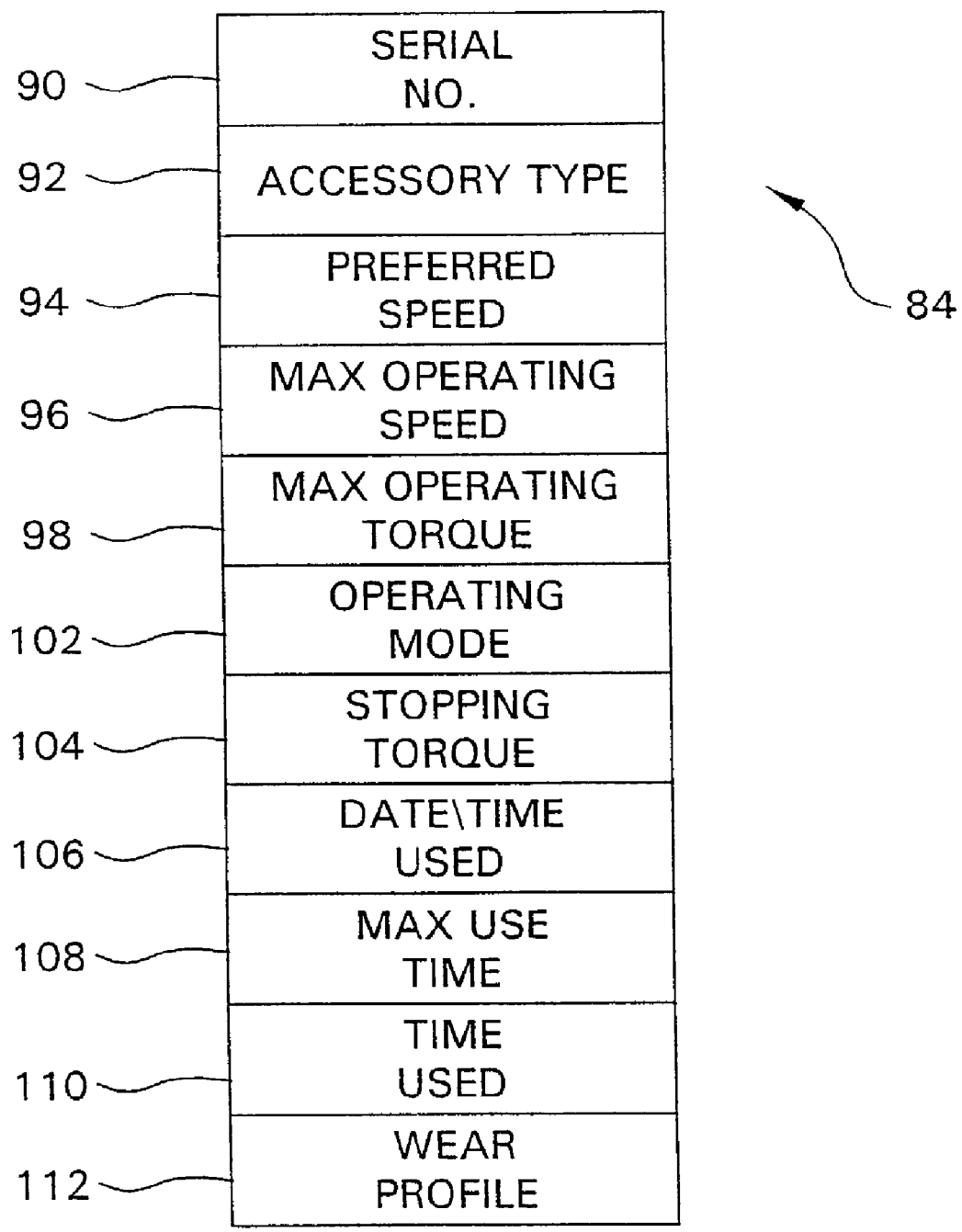
FIG. 4 depicts the contents of the memory internal to the cutting accessory.

FIG. 4 illustrates some of the different types of data stored in the tag controller/memory 84. These data include a serial number specific to the cutting accessory 24 with which tag 62 is integral, field 90. This number may also include a special authorization code, the purpose of which is described hereinafter. There is also a field with data that indicates cutting accessory's 24 type, field 92. For example, the data in field 92 may indicate that the cutting accessory is a burr that has a head with a particular diameter. Field 94 within controller/memory 84 contains data indicating a preferred speed at which the cutting accessory should be operated. Data indicating the maximum speed at which the cutting accessory should operate is contained in field 96. The maximum operating torque the cutting accessory should develop is indicated by data in field 98.

Field 102 contains data that indicates the preferred mode of operation of the cutting accessory. For example, if the cutting accessory 24 is a cutter, the most common mode of its operation is oscillatory. Alternatively, if the cutting accessory 24 is a burr, the preferred mode of operation is unidirectional. Stopping torque data is contained within a field 104. The stopping torque data is data used to regulate the deceleration of the handpiece motor 26.

Controller/memory 84 also contains data fields that are written to by the control console controller 70. One of these data fields is a date/time used field 106. Field 106 is used to store data indicating if and when the cutting accessory 24 was previously used. Specifically, during loading of basic information into the controller/memory 84, field 106 is loaded with flag data indicating that it has not been previously used. As described below, once the cutting accessory 24 is used, the controller 70 writes into field 106 an indication of when the use occurs.

A set of data indicating for how long the cutting accessory can be used is loaded into a MAX USE TIME data field 108 in controller/memory 84. This particular data represents how long a surgeon can expect to use the cutting accessory 24 before the cutting surfaces become worn to the level at which they may not efficiently cut tissue. The length of time contained in field 108 may be based on empirical studies indicating how long an accessory can be used before its cutting surfaces become excessively worn. The MAX USE TIME field 108 is loaded with data specifying this time period when the other permanent accessory-describing data are loaded into controller/memory 84. The controller/memory 84 also includes a TIME USED field 110. Data representative of the amount of time the cutting accessory has been used is stored in TIME USED field 110 by control console controller 70. A WEAR PROFILE field 112 contains data indicating the extent to which the cutting accessory has been worn during its use.

The system 20 of this invention is initially configured for operation by connecting the handpiece 22 to the control console 28. Controller 70 reads the data in the handpiece NOVRAM 32, stores these data in memory 69 and initially configures the system 20 to operate based on the data contained in the NOVRAM. Handpiece NOVRAM 32 also contains a data field, (not illustrated), that indicates whether or not the cutting accessories attached to the handpiece 22 may contain an identification chip 62. If this data indicates no such chip may be present, system 20 controls the actuation of the handpiece 22 based on the configuration data contained in NOVRAM 32.

Figure 5:
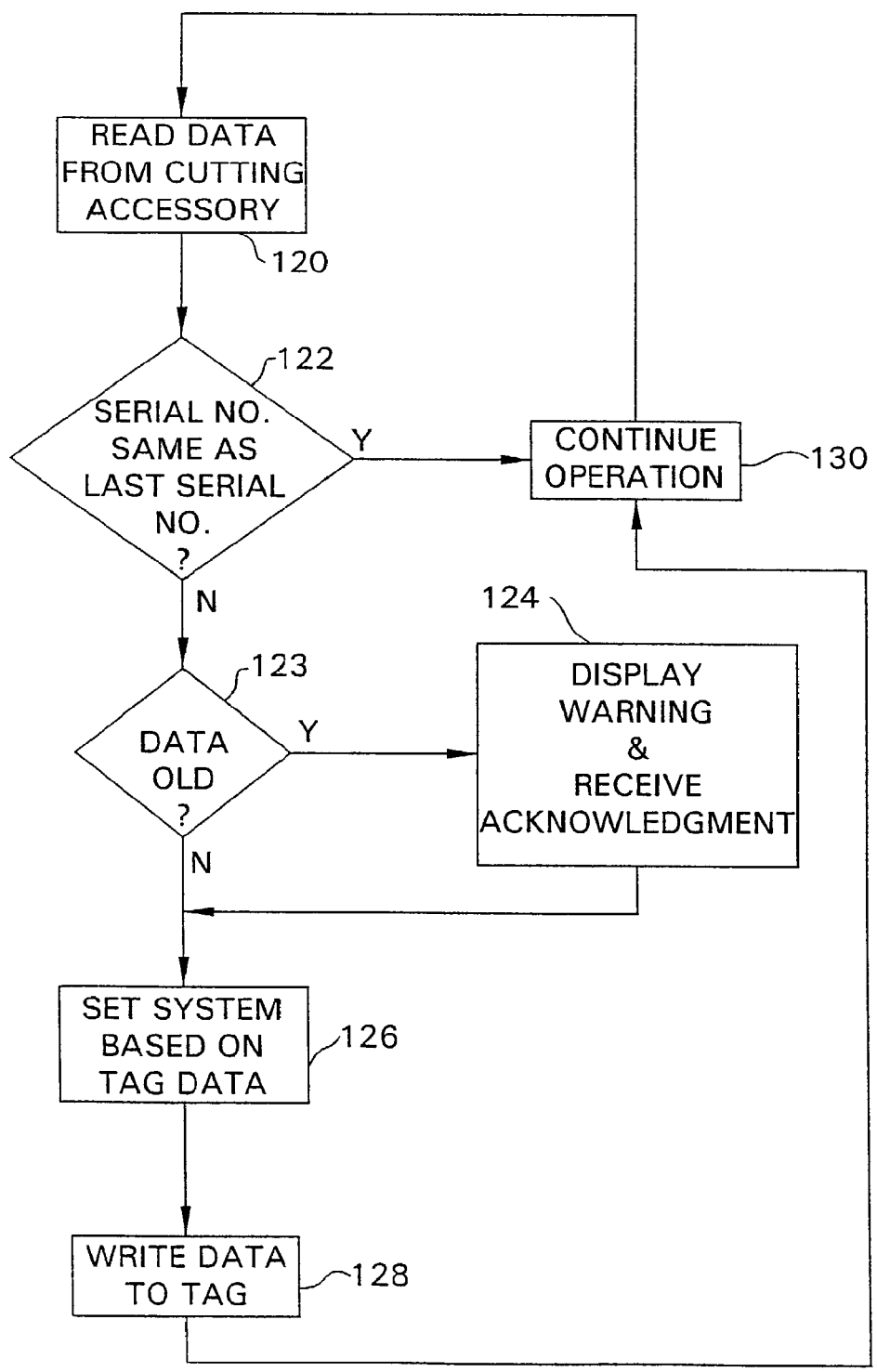
FIG. 5 is a block diagram of how the control console periodically reads the contents of the memory of the cutting accessory and reconfigures the operation of the system based on the retrieved data.

If, however, NOVRAM 32 indicates that the cutting accessory may contain a chip 62, controller 70 executes a read request, step 120 in FIG. 5, in which it reads the data in the chip controller/memory 84. In step 120, controller 70 generates a read request to chip 62. This request is converted into an ASK signal by modulator 74 and applied to the chip through coils 64 and 66. If a chip 62 is attached to cutting accessory 24, the chip, in response to the read request, writes out the stored data in its controller/memory 84 through coils 64 and 69 and demodulator 80 to controller 70. Controller 70 stores this data in appropriate fields within control console memory 69.

If the cutting accessory 24 does not include a chip 62, controller 70 does not receive any data in response to its read request. If this event occurs, controller 70 regulates the operation of the handpiece based on the data contained in NOVRAM 32, step not shown.

If cutting accessory chip 62 writes data to control console controller 70, the first thing the controller does is compare the serial number stored in chip 62 to the serial number stored from the last cutting accessory attached to the handpiece, step 122. If this is the first cutting accessory attached to the handpiece 22, the serial number the controller 70 has stored will be a set of flag data indicating that, previously, there was no attached cutting accessory with chip.

Once it has been determined that a new cutting accessory has been attached to the handpiece 22, step 122 may also include the sub-step of, determining based on the identification number, if the appropriate authorization code is present. If this code is not present the control console 70 may prevent further operation of the system with the attached cutting accessory 24 and/or generate a message on display 71 indicating that an unauthorized accessory is attached. (The sub-steps of this code determination and the steps executed when the code is not present are not illustrated.)

If the comparison of step 122 indicates that this is the first cutting accessory attached to the handpiece or, as discussed below, there has been a change in the cutting accessory attached to the handpiece, controller 70 reads and reviews the data read from the tag data/time used field 106. Specifically, in step 123, this data is reviewed to determine whether or not the cutting accessory was previously used and, if so, did the use occur at a date and time significantly before the current data and time. The data in chip 62 may indicate that there was no previous use of the cutting accessory. Alternatively, if the data indicates that the use of the cutting accessory was relatively recent, within, for example, 24 hours, controller 70 interprets this data as indicating that the use was in association with the current surgical procedure. Controller 70 interprets either of these two states as being ones in which use of the cutting accessory can continue normally.

However, in step 123, controller 70, based on the data read from field 108, may determine that the cutting accessory 26 was previously used at a time other than during the current surgical procedure. If this determination is made, controller 70 generates a warning message indicating this information on the console touch screen display 71, step 124. This provides the surgeon with an indication that the cutting accessory was used. In step 124, the controller presents a button on display 71 the surgeon must depress to acknowledge the used state of the cutting accessory before it allows the surgeon to actuate the handpiece 22.

Once it is determined that the cutting accessory 24 was not previously used, or the surgeon has acknowledged the previous use, controller 70 reconfigures the operation of the system, step 126. In step 126, based on the data read from the controller/memory 84 integral with the cutting accessory 24, controller 70 configures the system for operation with the cutting accessory. Specifically, the system 20 is set so that at least initially the handpiece motor will operate at the speed indicated by the data in preferred speed field 94. The forward/reverse/oscillate mode of the motor is set to that specified in operating mode field 102. Thus, in step 126, the data from the cutting accessory chip 62 is used to override data that supersedes the data in handpiece NOVRAM 32 that describes how the system should be configured. Not illustrated is the memory integral with controller 70 in which the data from chip 62 are stored and used as reference data to control the operation of the system 20.

In step 126, based on the data contained in the accessory type field 92, controller 70 causes console display 71 to present an indication of the accessory's type. Controller 70 further configures the system to prevent the surgeon for generating commands that allow the handpiece motor to be actuated at a speed greater than that specified in the maximum speed field 96. (Alternatively, controller 70 may simply require the surgeon to acknowledge a warning before allowing the surgeon to operate the handpiece above the maximum speed for the associated accessory 24.) System 20 is further configured by controller 70 to prevent the generation of energization signals from being applied to the handpiece motor that would cause the cutting accessory 24 to develop more torque than it is allowed to develop according to the data in maximum torque field 98. The system is further configured so that during deceleration of the handpiece motor, the motor will not be subjected to torque in excess of the braking torque specified in stopping torque field 106.

Controller 70 also updates the data in the controller/memory 84 of the cutting accessory 24, step 128. More particularly, in step 126, the date and time the cutting accessory 24 was attached to the handpiece 22 are written into the date/time used field 106.

Once steps 126 and 128 are executed, the system is ready for operation. The control console will, based on commands entered by the surgeon, apply energization signals to the handpiece motor 26 so that it will run in the appropriate mode and in appropriate speed for that attached cutting accessory 24. This operation of the system is represented by continued operation step 130 of FIG. 4.

Throughout the operation of the system 20, controller 70 will periodically execute read request/data read and serial number comparison steps 120 and 122, respectively. In some versions of the system, steps 120 and 122 are reexecuted once every 0.2 to 1.0 seconds during periods of time the handpiece is not being actuated. If the serial number comparison step 122 indicates that serial number associated with the cutting accessory 24 is unchanged, controller 70 recognizes this state as indicating that the same cutting accessory remains attached to the handpiece 22. If this condition is detected, controller continues to allow the system to operate in accordance with its current configuration; step 130 is continually executed.

However, serial number comparison step 122 may indicate that there has been a change in cutting accessory serial numbers since the step was previously executed. This condition is recognized by controller 70 as indicating that a different cutting accessory 24 is attached to the handpiece 22. If this is the detected system state, controller 70 reexecutes steps 123, 126 and 128, and, if necessary, step, 124, before reexecuting step continued operation step 128. When continuing operation step 128 is reexecuted, the system 20 has been reconfigured to actuate the handpiece in accordance with the characteristics of the newly attached cutting accessory 24.

Figure 6:
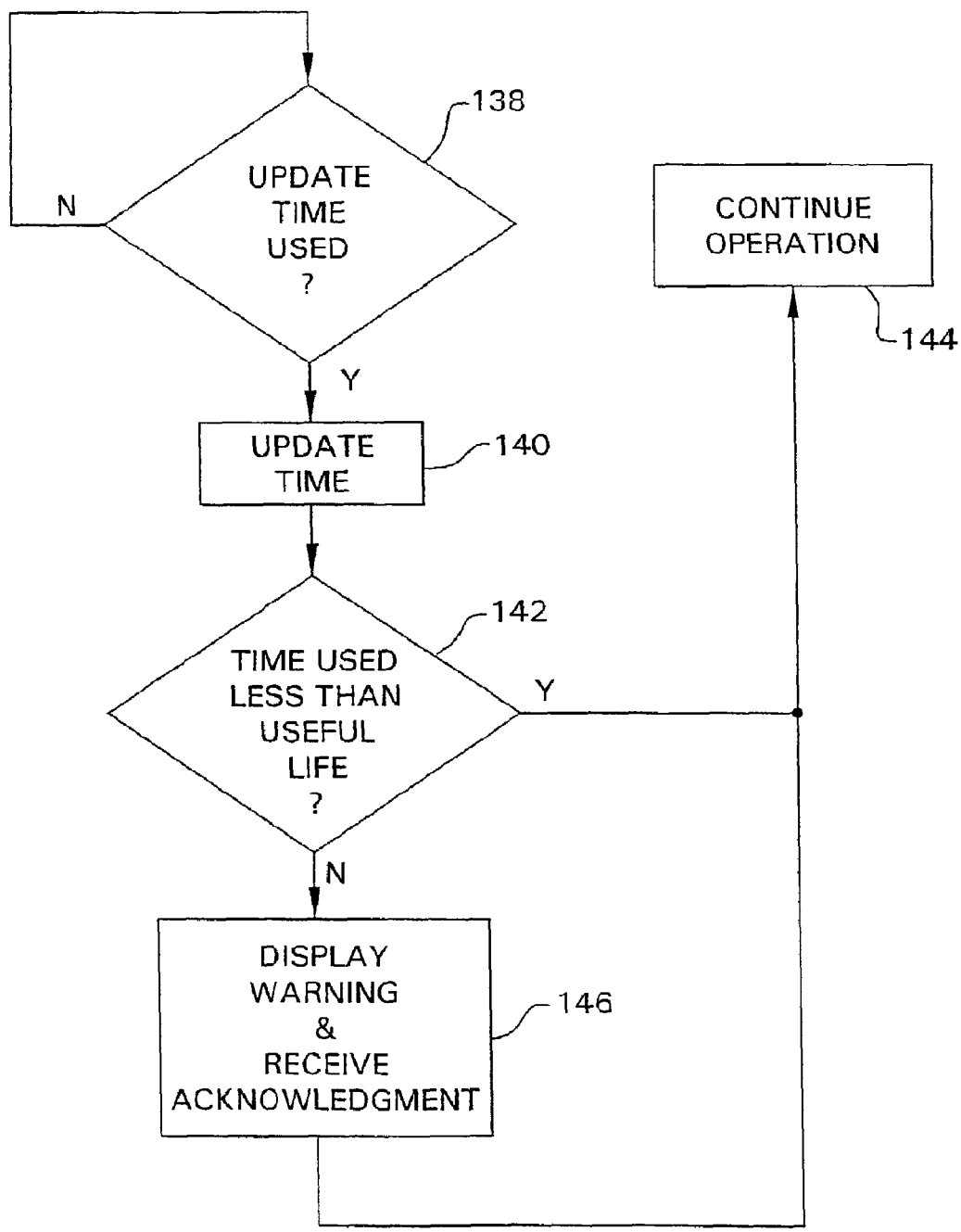
FIG. 6 depicts how the control console periodically determines whether or not a particular cutting accessory attached to the handpiece has been used for a time period equal to the useful lifetime of the handpiece.

Controller 70 also monitors the amount of time the cutting accessory 24 is actuated. Specifically, controller 70 maintains an internal timer in which a time count is maintained indicating how long the cutting accessory attached to the handpiece 22 is actuated. In some versions of the invention, after each time the motor is deactivated, step 138 of FIG. 6, the controller 70 performs this monitoring. Specifically, after the motor is deactivated, controller 70 performs a step 140 in which the controller writes into the TIME USED field 110 of the cutting accessory controller/memory 84 data indicating the total time the cutting accessory has been used. These data are determined based on the data read from the TIME USED field 110 when the cutting accessory was first attached to the handpiece as well as the elapsed time of use for the accessory stored by the controller 70. This step 140 may be integrated into the first reexecution of step 120 after the motor is deactivated. Alternatively, step 140 may be executed as a separate write data step after the motor is deactivated. As part of step 140, the elapsed time count held by the internal timer is zeroed out.

Controller 70 then determines if the total time the cutting accessory has been used is less than the time period specified in the MAX USE TIME field 108 of the cutting accessory 24, step 142. In some versions of the invention, it is believed the useful lifetime for a cutting accessory will be between, for example, 30 and 120 minutes. If the total use time is less than the maximum recommended use time, controller 70 allows the system to operate as before, step 144. If, however, the total time of use is greater than the specified maximum recommended use time, controller 70 presents a warning notice and an acknowledgement button on the touch screen display, step 146. The surgeon must acknowledge that the cutting accessory 24 has been used for a time greater than its specified maximum use before the controller allows the system to continue to actuate the cutting accessory 24.

Chip 64 of cutting accessory 24 of this invention contains a significant amount of data that describes the operating characteristics and state of the cutting accessory. The control console 28 of this system automatically both reads this data and periodically updates it. The control console 28, based on the data read from chip 64, configures the system so it will operate in an appropriate manner given the specific characteristics of the specific attached cutting accessory. Specifically, the control console controller 70 configures the system so that, at least initially the handpiece motor will run at the preferred speed and in the preferred mode for the cutting accessory. The system is also configured to prevent the cutting accessory from being driven above its specific maximum operating speed, from developing torque beyond its design limit and from being subjected to excessive braking torque. This configuration of the system occurs without human intervention. Consequently, the possibility that human error could result in the incorrect configuration of the system 20 for the cutting accessory 24 attached to it is substantially eliminated.

The system of this invention provides the surgeon with an indication of whether or not the cutting accessory attached to it was previously used. This provides the surgeon with an indication that the cutting accessory may be worn and, therefore, will not be able to satisfactorily perform the intended surgical procedure.

System 20 of this invention also, during the surgical procedure, provides the surgeon an indication that a cutting accessory has been used for a period equal to its intended lifetime. This information is supplied to the surgeon to inform him/her that the cutting accessory, even if new when installed, may be worn to the level of reduced efficiency. Thus, the surgeon, upon receiving this information, can decide whether or not to continue using the current accessory or replace it with a new one.

Moreover, the handpiece 22 of this invention is constructed so that ring 67, which functions as the inner wall in which coil 66 is contained is plastic and the handpiece housing 34, which forms the outer containment wall for the coil, is formed of metal. As a result of this construction, the inductive field generated by coil 66 is localized within the cavity in the distal end of the housing 34 in which cutting accessory 24 is seated. The inductive field generated by coil 66 does not extend beyond the surface of housing 34. This substantially eliminates the possibility that if the handpiece of this invention was placed on a surface next to a cutting accessory that is provided with an identification chip 64, the handpiece coil 66 will not establish an inductively coupled circuit so as to provide the control console 28 with a false indication that the handpiece is actually connected to the adjacent cutting accessory.

It should be recognized that the foregoing description has been limited to one preferred version of the invention. Other versions of the invention may vary from what has been described. For example, in some versions of the invention, the coils integral with the cutting accessory and handpiece may not extend circumferentially around the longitudinal axis of these components. Instead, these coils may be positioned to be aligned longitudinally with the longitudinal axes of the cutting accessory and handpiece.

Also, in some versions of the invention, the handpiece may be constructed so that the material in which coil 66 is encased is metal. Thus, in these versions of the invention, the presence of coil 66 does not require the handpiece to have a non-metallic component that is directly exposed to the rigors of sterilization.

Moreover, the data contained within the chip 62 of the handpiece may vary from what has been described. For instance, in some versions of the invention, the handpiece of the invention may not include a NOVRAM. In these versions of the invention, chip 62 contains all, or substantially all, of the handpiece characteristic data that was otherwise stored in the handpiece NOVRAM. This data is, however, specific to the operating characteristics of the cutting accessory 24 with which the chip 62 is integral. Once the cutting accessory 24 is attached to the handpiece 22, controller 70 configures the system based on the data read from the chip 62.

Also, in some versions of the invention, it may not be possible for the cutting accessory to overwrite new data into any data field. In these versions of the invention, the chip 62 has empty data fields when it is installed in the cutting accessory 24. Then, during operation of the system 20, controller 70 writes the new data that needs to be written into chip 62 into the previously empty controller/memory data fields. During the read out of the contents of the controller/memory 84, step 120, all the data are read out. The controller is configured to recognize the last data in a set of data fields, for example in a set of time used fields, as being the most current version of the data.

Figure 7:
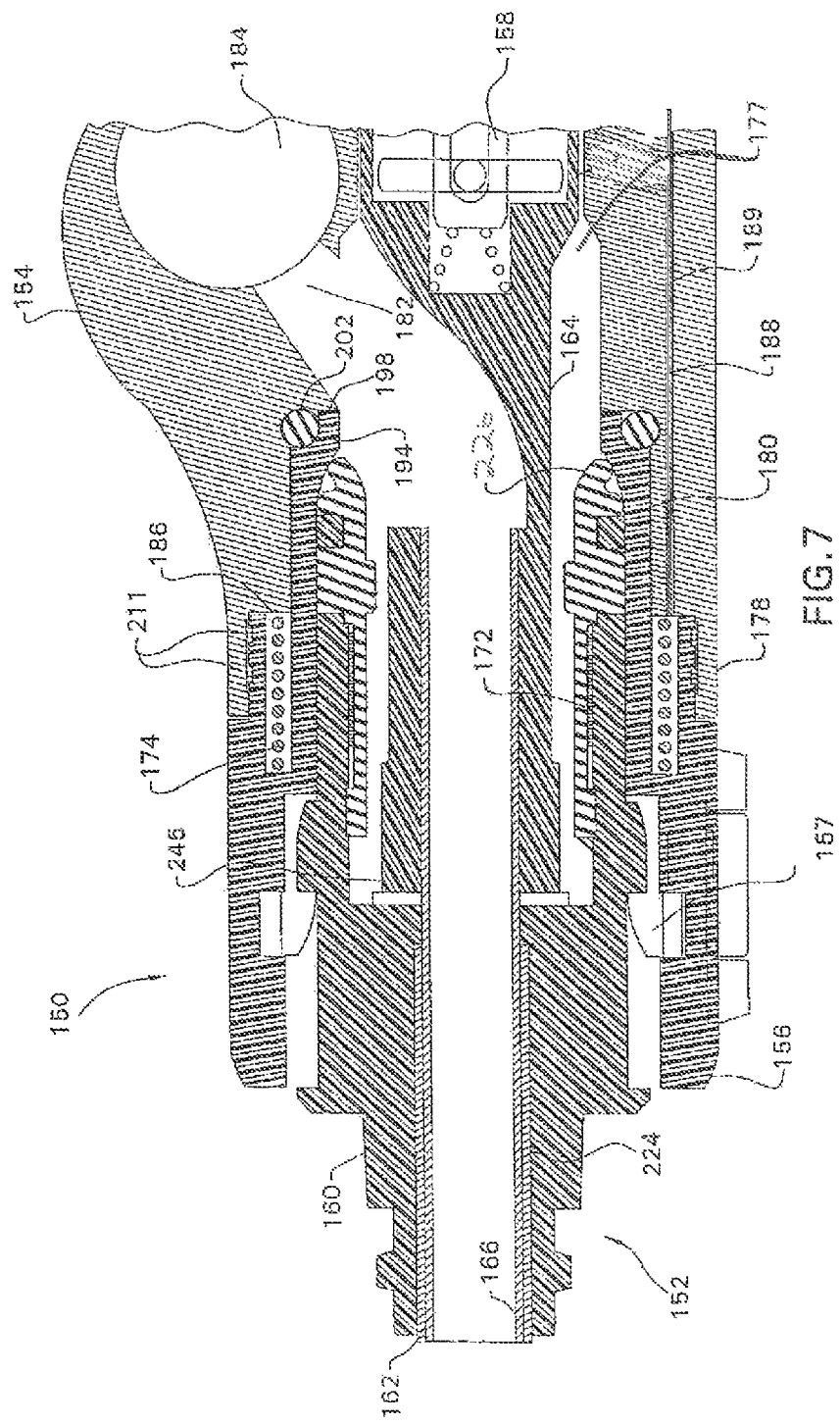
FIG. 7 is a cross-sectional view of an alternative handpiece and cutting accessory of this invention.

FIG. 7 depicts an alternative handpiece 150 and cutting accessory 152 constructed in accordance with this invention. Specifically, the handpiece 150 has a metal body 154 to which a plastic locking collet 156 is attached. Internal to the body is a motor, not illustrated, from which a drive shaft 158 extends.

The cutting accessory 152 has a static hub 160 that is releasably held to the handpiece 150 by a locking assembly mounted in the locking collet 156. The locking assembly, while not fully illustrated, includes a tongue 157 that is releasably seated in a recessed surface of hub 160. A tubular housing or outer tube 162 extends from hub 160. Located proximal to hub 160 and within the handpiece 150 is a drive coupler 164. Drive coupler 164 has a proximal end designed to engage a coupling member integral with drive shaft 158 so that the shaft and coupler rotate in unison. A drive shaft, or inner tube 166 is secured and extends distally from the drive coupler 164. The drive shaft 166 extends through hub 160 and into housing 162.

Figure 11A:
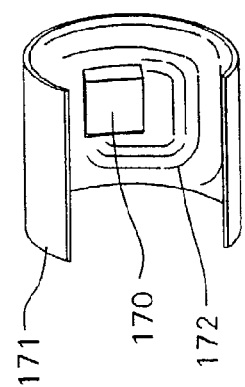
FIG. 11A is a perspective view of the cutting accessory tag assembly.

An RFID chip 170 (FIG. 11A) is secured to hub 160. A coil 172 is connected to chip 170. A coil 174 is mounted to handpiece body 154. Handpiece coil 174 inductively exchanges signals with chip 170 through coil 172.

Handpiece body 154 is generally elongated in shape and has elongated bore 177. Bore 177 is the space in which the handpiece motor as well as the proximal end of the cutting accessory 152 are seated. The distal end of body 154 is shaped to have a ring shaped head 178 that defines a counterbore 180 that opens into bore 177. Counterbore 180 opens into a main bore in which the motor is housed. A suction bore 182 branches off of bore 177. Suction is drawn through the cutting accessory 152 through the suction bore 182. Partially seen in FIG. 7 is a valve bore 184 that interests the suction bore. A valve (not illustrated,) is disposed in the valve bore 184, for regulating the suction flow through the cutting accessory 152 and the handpiece 150.

Handpiece body 154 is further formed so that the distal end portion of the inner wall of head 178 has an inwardly directed step 186. Coil 174 is disposed in the space defined by step 186. In some versions of the invention, coil 174 is in the helical wrap of wire. The wire may be wrapped around a thin film of polyamide material that supports the wire. In alternative versions of the invention, coil 174 is formed on flex circuit. The flex circuit is placed in the space adjacent step 186.

Conductors 188 that connect coil 174 to downline components in the handpiece 150 are seated in a separate bore 189 formed in the housing body 154. Specifically, internal to the handpiece is an impedance matching circuit that establishes the impedance of the circuit internal to the handpiece to 50 Ohms to facilitate the exchange of the signals between control console 28 and coil 174 over a 50 Ohm impedance coaxial cable.

Figure 8:
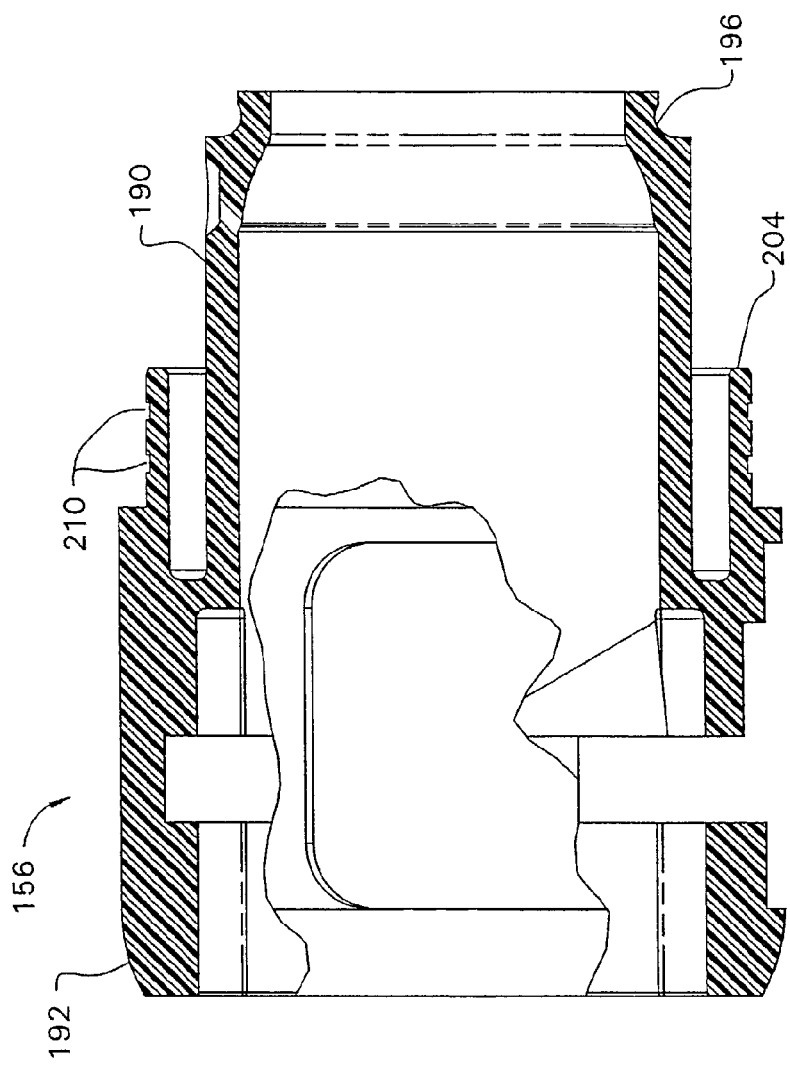
FIG. 8 is a cross-sectional view of locking collet of the handpiece of FIG. 7.

Locking collet 156, seen best by reference to FIG. 8, has a tubular base 190. Extending distally from base 190, collet 156 is shaped to have a head 192 that has a larger outer diameter to base 190. The moving components of the locking assembly that engage hub 160 are mounted in base 190.

When the handpiece 150 is assembled, collet base 190 is fitted in counterbore 180 so that the outer wall of the base abuts the inner wall of body proximal to step 186. An O-ring 194 is located around the interface where the proximal end of collet base 190 abuts the handpiece body 154. Specifically, the collet base 190 is formed to define a groove 196 that extends circumferentially around the distal end of the outer perimeter of the proximal end of the base 190. In order to provide structural strength for the collet, it will be observed that the proximal end is located inwardly of the more distal sections of the base. The handpiece body is shaped to define an annular stepped surface 198. The stepped surface is the surface from which the body head 178 extends. Stepped surface 198 is the surface against which the proximal facing end of collet base 190 extends. Housing body 154 is further formed so that there is a small grooved surface 202 within stepped surface 198. Specifically, grooved surface 202 extends annularly around stepped surface 198 adjacent the outer perimeter of the stepped surface. The O-ring 194 is thus seated in the grooved surface 202 of the handpiece body 154 and groove 196 of collet 156.

Locking collet 156 is further formed to have a generally cylindrical outer ring 204 that extends proximally from head 192. Outer ring 204 thus extends circumferentially around and is spaced away from the distal end of locking collet base 190.

When the handpiece 150 is assembled, coil 174 is seated in the annular space between the outer wall of collet base 190 and the inner wall of outer ring 204. In other words, this annular space forms an enclosure for holding coil 174. The collet 156 is fitted to body 154 so that the outer surface of collet outer ring 204 is disposed against the inner wall of the base head 178.

As part of the process of assembling the handpiece 150, an adhesive, such as a silicone adhesive, is placed between the opposed surfaces of the body head 178 and collet outer ring 204. A fraction of this adhesive collects in two annular channels 210 formed in the handpiece body head 178. Upon the curing of this adhesive in the channels, the adhesive forms two O-rings 211 between the body 154 and collet 156. These O-rings 211 thus prevent fluid flow from outside the handpiece 150 to coil 174.

Figure 9:
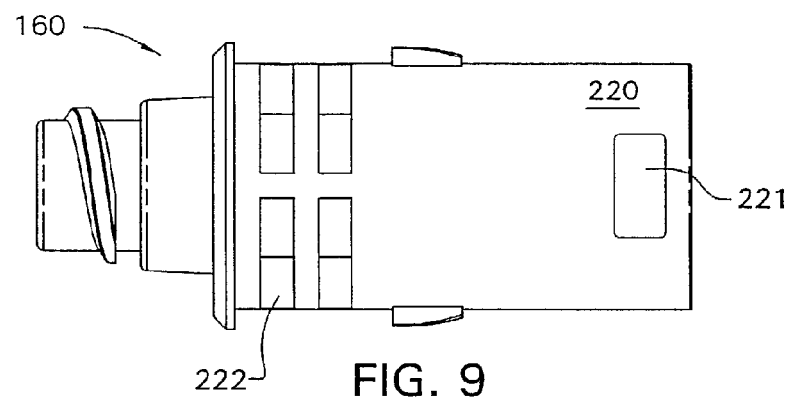
FIG. 9 is a plan view of the hub of the cutting accessory of FIG. 7.
Figure 10:
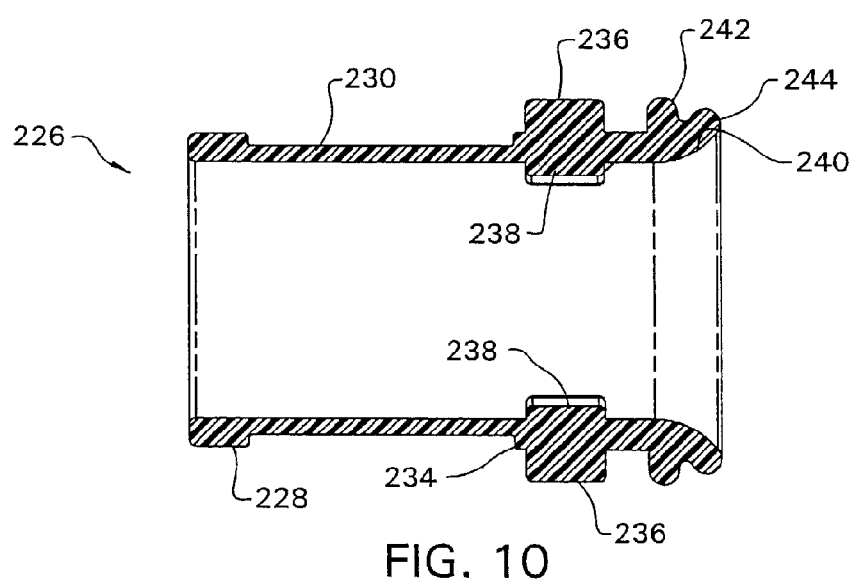
FIG. 10 is a cross-sectional view of the coil seal of the cutting accessory of FIG. 7.
Figure 11:
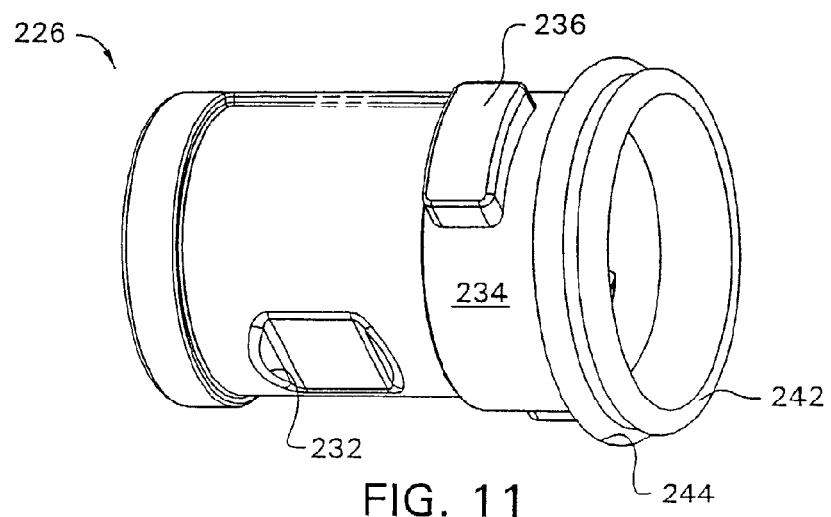
FIG. 11 is a perspective view of the coil seal of the cutting accessory of FIG. 7.

Hub 160, which is formed of rigid plastic, is now described by reference to FIG. 9. The hub 160 is constructed to have a sleeve-shaped base 220. The base 220, it will be observed, is formed with two diametrically opposed, generally rectangularly shaped openings 221. Extending forward from base 220 and formed integrally therewith is a substantially solid head 222. While head 222 is substantially solid, the hub 160 is formed so that a bore 224 extends axially through the head. Housing 162 is mounted in bore 224 in any conventional manner to extend forward from head 222.

A generally tube-shaped coil seal 226 is disposed in hub base 220. Coil seal 226 is formed from flexible sterilizable material. In one version of the invention, coil seal 226 is formed from a silicon rubber that has 55 Shore A durometer hardness. The coil seal 226 is shaped so as to have a first distal end section 228 that has a constant outer diameter and inner diameter. Extending proximally from the distal end section 228, the coil seal 226 has a main section 230. Main section 230 has the same inner diameter as distal end section 228 and a smaller outer diameter. The coil seal is further formed so as to define a generally rectangular recess 232 in the outer surface of main section 230. Located proximal to main section 230, the coil seal 226 has a locking section 234. The inner and outer diameters of locking section 234 are the same as those of the distal end section 228.

The locking section 234 of the coil seal is further formed to have two diametrically opposed lock tabs 236. Each lock tab 236 extends radially outwardly from the outer surface of the locking section 234. The locking section also has two diametrically opposed stop tabs 238 that extend inwardly from the inner wall of the lock section. In the depicted version of the invention, each stop tab 238 is radially aligned with a separate one of the lock tabs 236.

Coil seal 226 is further formed to have a tail section 240 that extends rearwardly from the locking section and that forms the proximal end of the seal. The tail section 240 is formed to define two annular spaced apart ribs 242 and 244 that extend circumferentially around coil seal 226. Both ribs 242 and 244 extend beyond the outer diameter of the seal locking section 234. In the depicted version of the invention, the diameter of the circle subtended by the more proximal of the two ribs, rib 244, is less than the diameter subtended by the other rib, rib 242. Tail section 240 is further formed to have an inner wall that is outwardly flared.

When a cutting accessory 152 of this version of the invention is assembled, the RFID chip 170 is seated in seal recess 232. Coil 172 is wound over the reduced diameter outer surface of seal main section 230. In some versions of the invention, seen in FIG. 11A, the chip 170 is mounted on a small flex circuit 171; the coil 172 is a conductive trace formed on the flex circuit 171. After manufacture of the flex circuit 171, the flex circuit, with the chip 170 mounted thereon, is wrapped in cylinder over seal main section 230.

The RFID chip-coil-and-seal assembly is fitted in hub base 220. Thus both the RFID chip 170 and coil 172 are disposed between the inner wall of the hub base and the outer surface of coil seal 226. Owing to the relative dimensions of hub 160 and coil seal 226, the outer surfaces of the seal distal end and locking sections 228 and 234, respectively, press against the inner wall of the hub base 220. This contact forms a seal around chip 170 and coil 172. Thus, in most preferred versions of the invention, there is no need to employ an adhesive or other chemical to provide a moisture barrier around the chip 170 and coil 172.

As part of the insertion of the coil seal 226 into the hub 160, lock tabs 236 are seated in hub base openings 221. The seating of the lock tabs 236 in openings 221 serves to hold the coil seal 226 to the hub 160.

When the coil seal 226 is so attached to hub 160, tail section ribs 242 and 244 are located proximal to the proximal end of the hub. When the assembled cutting accessory 152 is fitted in the handpiece 150, ribs 242 and 244 abut the inwardly flared surface of the handpiece collet base 190. The ribs thus function as a seal that prevents leakage from the suction channel to the coil cavity or the outside environment.

It will further be observed that the distal end of driver coupler 164 is formed with a head 245 that has a relatively large outer diameter. When cutting accessory 152 is assembled, the driver coupler and rotating shaft subassembly is moved past coil seal 226 in hub bore 224. Owing to the dimensioning of the components, the drive coupler head 245 abuts the coil seal stop tabs 238. Owing to the compressibility of the material from which the coil seal is formed, a small amount of force will compress the stop tabs 238 to allow the complete insertion of the drive coupler and rotating shaft. After assembly, if the cutting accessory 152 is held vertically, the drive coupler head 245 abuts the stop tabs 238. Thus, the stop tabs prevent gravity, without any additional force, from causing the driver coupler and rotating shaft to drop out of hub 160.

Figure 12:
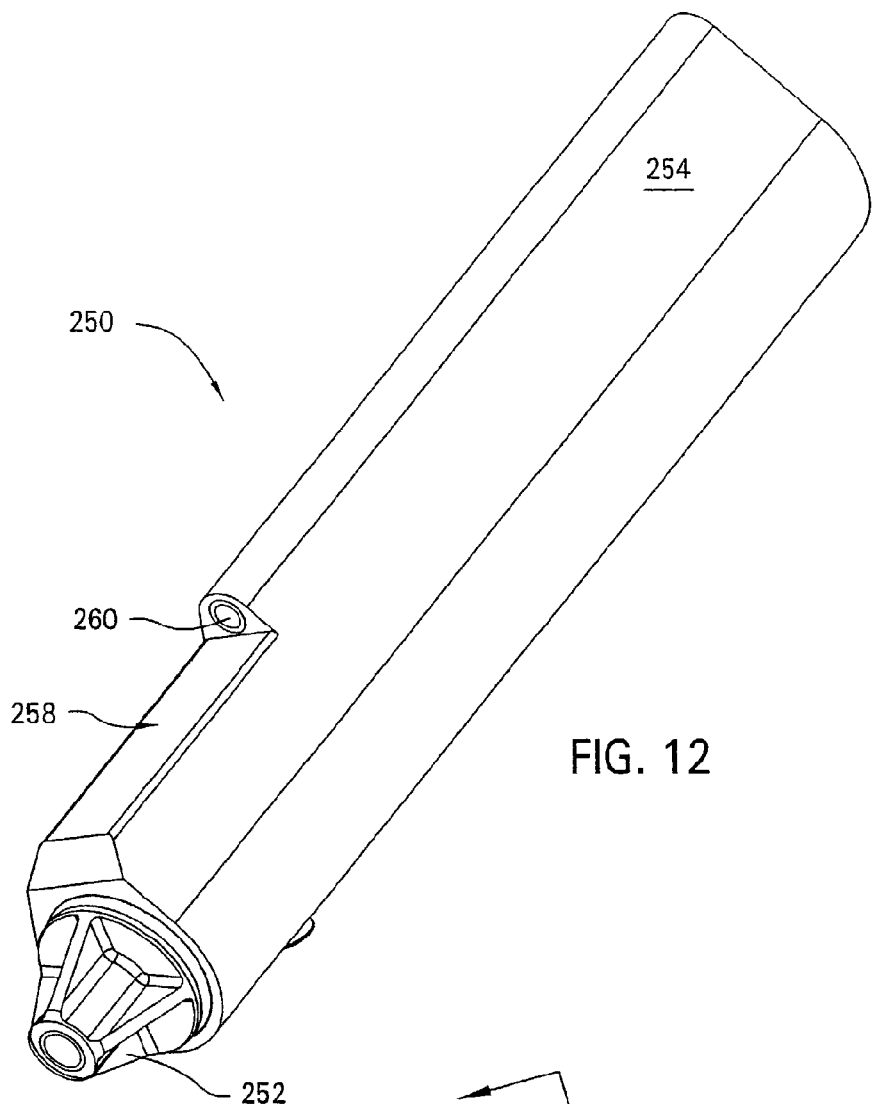
FIG. 12 is a perspective view of a partially assembled alternative handpiece of this invention in which a cutting accessory hub is shown coupled to the handpiece.
Figure 13:
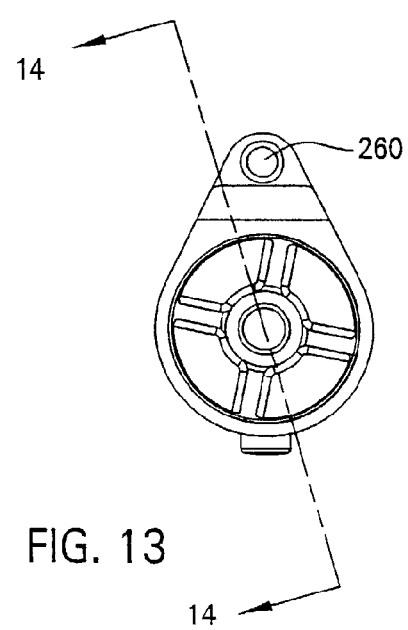
FIG. 13 is a front view of the handpiece and cutting accessory hub of FIG. 12.
Figure 14:
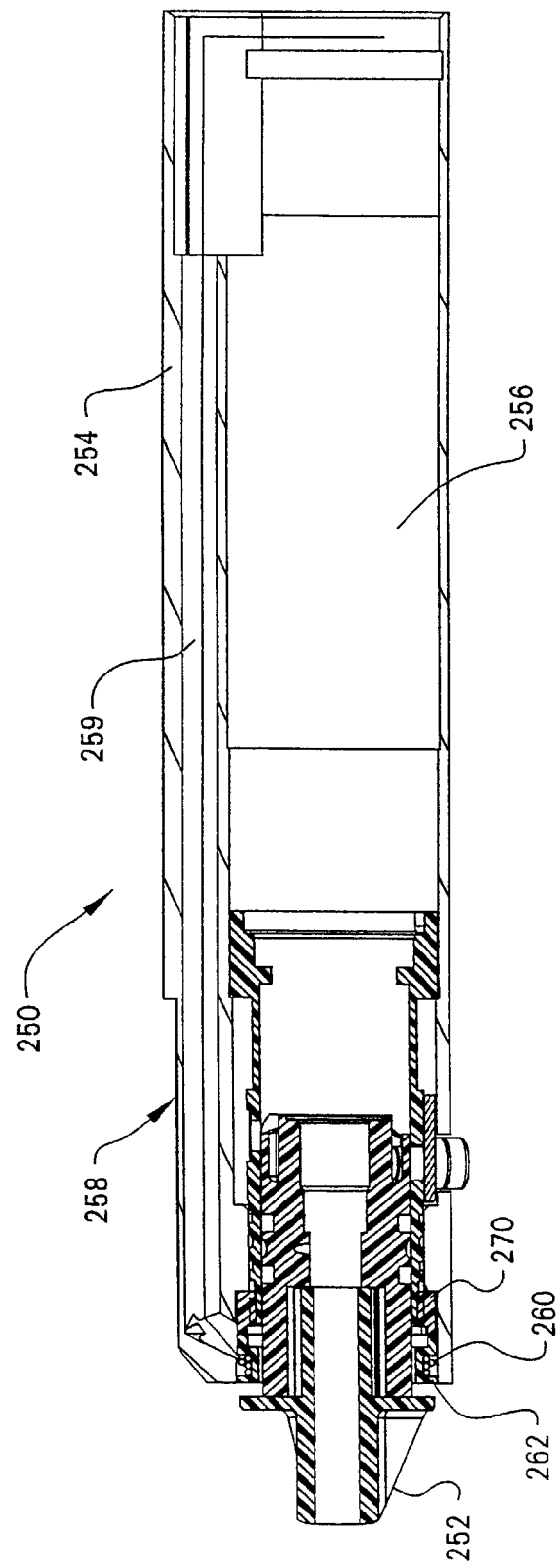
FIG. 14 is a cross sectional view of the handpiece and cutting accessory hub taken along line 14-14 of FIG. 13.

FIGS. 12, 13 and 14 illustrate an alternative handpiece 250 and cutting accessory hub 252 of this invention. The handpiece 250, shown in cross-section in FIG. 14, includes an elongated body 254 that has an axially extending bore 256. The center and proximal end sections of bore 256 serve as the space in which the motor and cable connector integral with the handpiece 250 are housed, (motor and cable connector not shown). The distal end section of bore 256 is the space internal to the handpiece in which the cutting accessory hub and drive coupler are received, (drive coupler not shown).

This particular handpiece has a motor with a cannulated rotor. Thus, suction is drawn axially from the distal end of the rotating shaft of the attached cutting accessory, through the drive coupler and the motor rotor by the suction pump attached to the handpiece. Irrigation fluid is supplied to an opening in the hub 252. The irrigation fluid can also be directed through the rotating shaft. A valve in the proximal end of body bore 256 selectively connects the rotating shaft to either the suction pump or the source of irrigating fluid. This valve is set by a control tab, (not illustrated), that is positioned above a stepped surface 258 formed in the outside of body 254. The control tab displaces a linkage rod (not illustrated), that is seated in a rod bore 259 formed in the body 254. The Applicant's Assignee's U.S. patent application, SYSTEM AND METHOD FOR PERFORMING IRRIGATED NOSE AND THROAT SURGERY Ser. No. 60/395,881, filed on Jul. 13, 2002, now U.S. Pat. No. 7,318,831 B2, and incorporated herein by reference, provides further details of the above features of this handpiece.

Figure 15A:
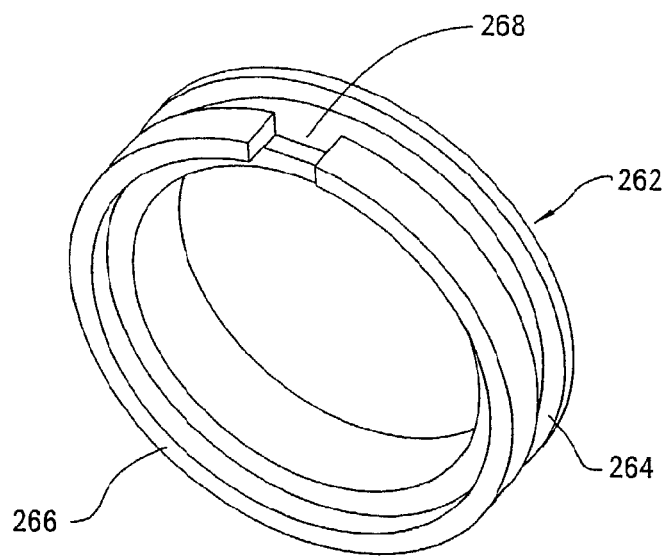
FIGS. 15A and 15B are, respectively, perspective and cross sectional views of the handpiece coil housing.
Figure 15B:
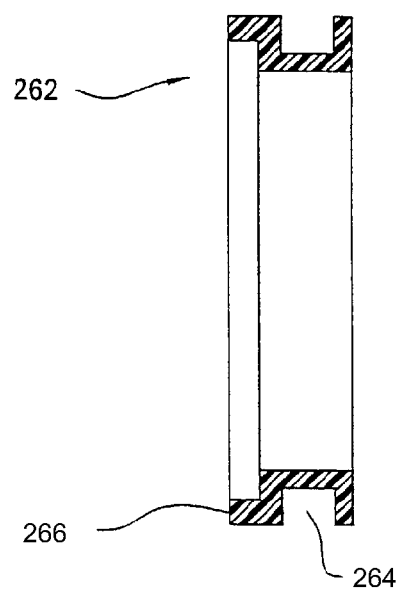

A coil 260 is disposed in the distal end of body bore 256, immediately inside the distal end opening of bore 260. Coil 260, shown in FIG. 14 as a wrap of wires, is contained in a coil housing 262, now described by reference to FIGS. 15A and 15B. The coil housing 262 is formed from a plastic cable to withstand sterilization such as PEEK plastic and is generally ring-shaped. Coil housing 262 is further formed to define a rectangular groove 264 that extends circumferentially around the outside of the housing. Groove 264 is the space in which coil 260 is seated. The proximal facing end of the coil housing 262 is formed to have an annular lip 266 that extends substantially circumferentially around the housing. Lip 266 has an outer diameter substantially equal to the outer diameter of the more distal portions of the coil housing. The inner diameter of lip 266 is greater than that of the rest of the housing 262.

Coil housing 262 is further formed to have a slot 268 that is defined by opposed spaced apart ends of lip 266. The wires forming coil 260 extend proximally into the handpiece body through slot 268.

When handpiece 250 is assembled, coil 260 is seated in housing groove 264. The coil-and-housing assembly is seated in the distal end of body bore 256. In some versions of the invention, the coil housing 262 is adhesively secured to a lock nut 270 disposed in body bore 256. Alternatively, coil housing 262 may be provided with feet that press fit, snap fit or key-in-key hole slot fit into the lock nut. In some versions of the invention, the coil housing 262 may even press fit into body bore 256.

The conductors connected to coil 260 extend proximally, rearwardly, from the coil and are disposed in a bore, signal conduit 259, formed in the handpiece body 254. Signal conduit 259, it is observed from FIG. 14, extends generally parallel to bore 256. The distal end of signal conduit 259 extends diagonally into the section of bore 256 in which coil housing lip 266 is seated.

In one version of the invention, the conductors that extend to coil 260, as well as the conductors that actually form the coil, are formed on a flex circuit 272 now described by reference to FIG. 16. Flex circuit 272 is formed of polyamide or any other material that can serve as a structural substrate for conductors and electrical components. Flex circuit 272 has a first section, section 273 that is vertical in the Figure. A second section, section 284, extends away from the distal end of first section 273 such that the longitudinal axes of flex circuit sections 273 and 284 are angularly offset from each other. In the depicted version of the invention, the flex circuit sections 273 and 284 are angularly offset by 90° so the flex circuit 272 is L-shaped. Conductive traces 274, 276 and 278 are formed on the flex circuit 272. Two traces, traces 274 and 276 are parallel and are located on the first section 273 of the flex circuit in FIG. 16. An integrated circuit 280 is shown attached to trace 276. Circuit 280 is an impedance matching circuit to bring the impedance of the circuit on the trace to 50 Ohms. While not illustrated, it should be recognized that trace 274 is also attached to the integrated circuit 280. Trace 274 also terminates a short distance above integrated circuit 280.

Figure 16:
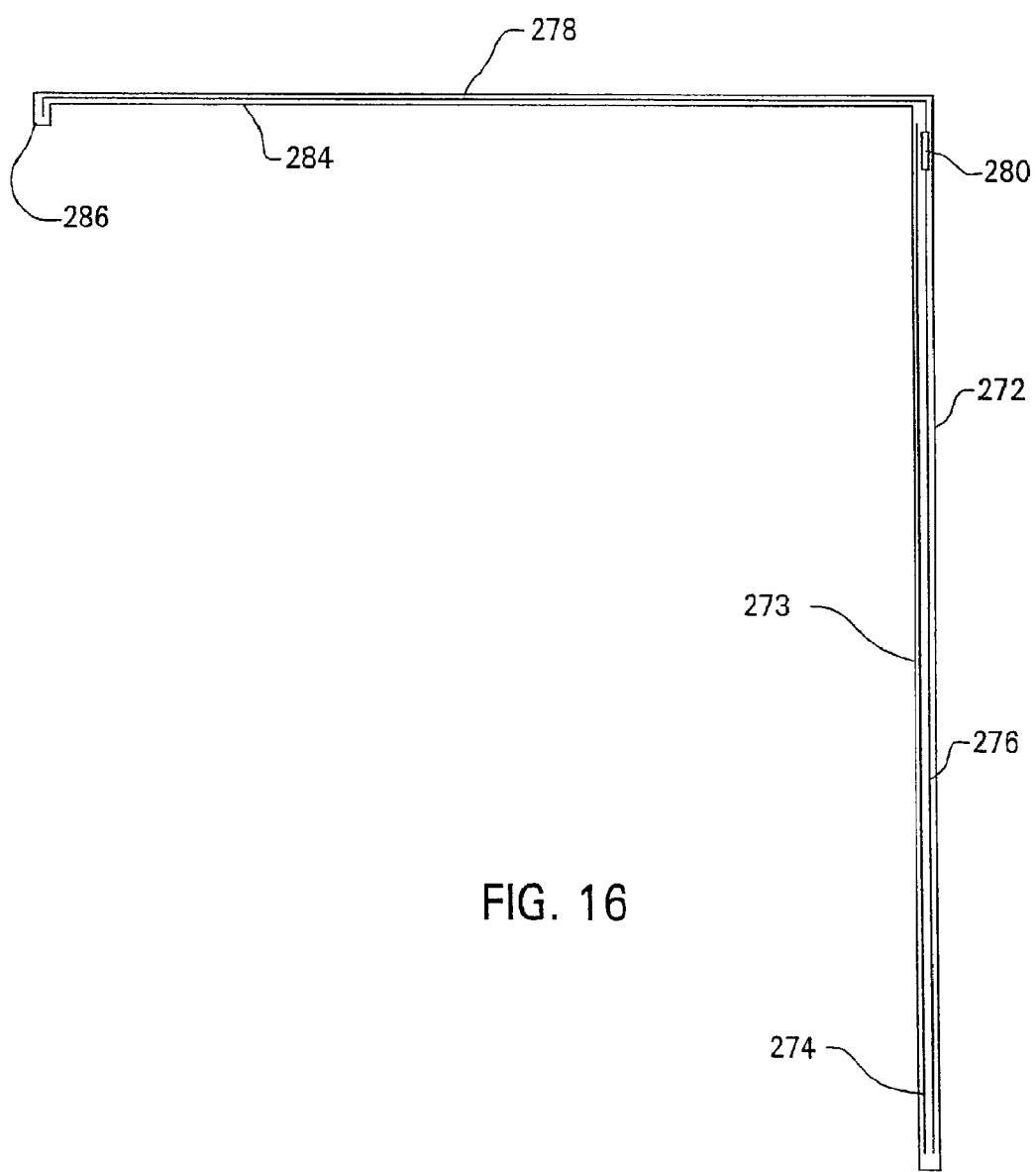
FIG. 16 is a plan view of one coil assembly of this invention.

Trace 278 extends from integrated circuit 280 and is the conductive trace formed on the second section 284 of flex circuit 272 in FIG. 16. The flex circuit 272 is further formed to have a small branch section 286 that extends diagonally downward from the end of the second section 284 opposite the first section 273. The free end of trace 278 is formed over the branch section 286.

When a version of the invention incorporating flex circuit 272 is assembled, second section 284 of the flex circuit is wrapped in a circular pattern at least once in coil housing groove 264. More specifically, the flex circuit 272 is wound in a closed circular shape around the coil housing 262 so that flex circuit branch section 286 extends over first section 273. Then, the free end of trace 278 is soldered or otherwise conductively connected to the free end of trace 274. Thus trace 278 forms the handpiece coil.

Figure 17:
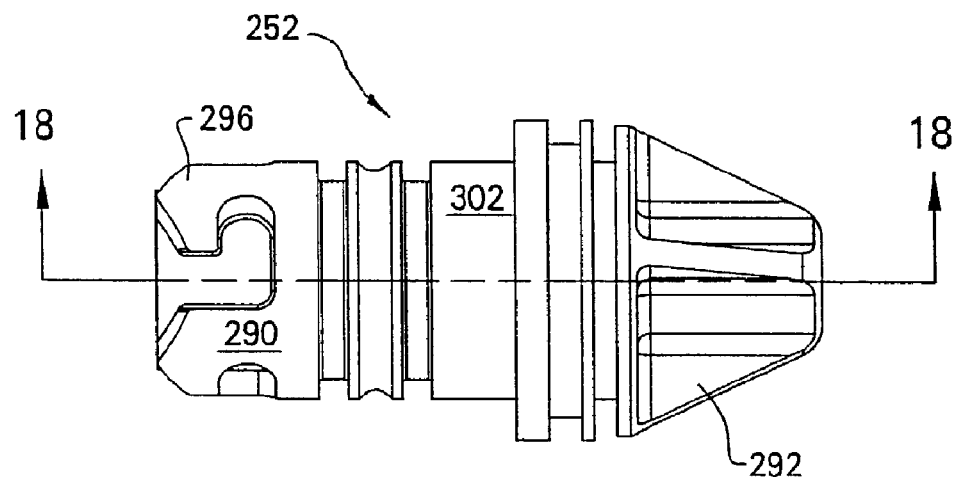
FIG. 17 is a plan view of the outer hub of FIG. 12.
Figure 18:
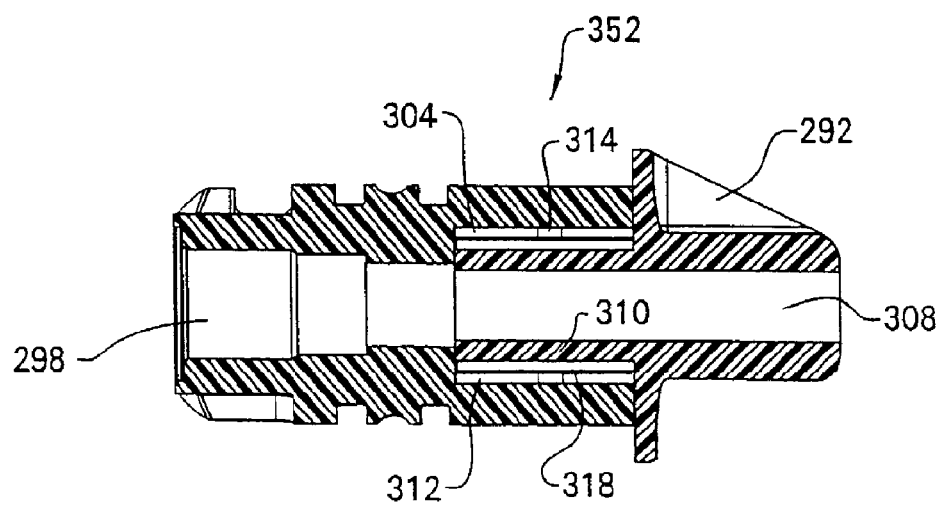
FIG. 18 is a cross sectional view of the outer hub taken along line 18-18 of FIG. 17.

The cutting accessory hub 252, now described by reference to FIGS. 17 and 18, is formed from two plastic pieces, base 290 and head 292. Base 290 is formed to have a proximal section 296 that has a multisection axial bore 298. It should be understood that bore 298 is dimensioned to receive the drive coupler and proximal end of the rotating shaft of the cutting accessory with which hub 252 is integral. Base 290 also has a distal section 302 integrally formed with and located forward of proximal section 296. Base distal section 302 is formed to have a counterbore 304 that has a diameter that is larger than the diameter of the adjacent section of bore 298.

The hub head 292 is formed to have an axially extending through bore 308. Bore 308 is dimensioned to receive the associated rotating shaft. The hub head is shaped to have a generally cylindrical, proximally located stem section 310. Collectively the components forming hub 252 are shaped so that stem section 310 has an outer diameter that is appreciably less than the inner diameter of base distal end section 302.

Figure 19:
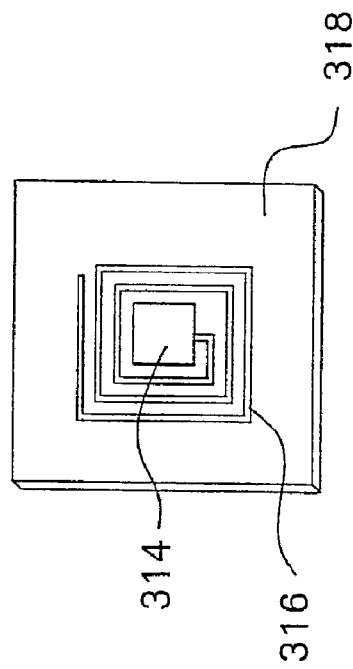
FIG. 19 is a perspective view of a chip-and-coil subassembly, a tag, of this invention.

When hub 252 is assembled, head stem section 310 is seated in base counterbore 304. Owing to the relative dimensions of the base 290 and head 292, when these components are so assembled an annular coil space 312 is formed between stem section 310 and the adjacent end wall of base distal end section 302. An RFID chip 314 and coil 316, now described by reference to FIG. 19 are seated in this space. Specifically, the chip 314 and coil 316 are assembled as a single unit on a flexible substrate 318. Often this assembly is referred to as a tag. A chip from the Philips Semiconductor of Netherlands i.Code family of chips can be employed as the chip 314. Conductive traces that form coil 316 are formed on substrate 318. As part of the hub assembly process, prior to the insertion of head 292 over base 290, substrate 318 is wrapped into a cylindrical shape and inserted in base counterbore 304. The head stem section 310 is then seated in counterbore 304. It will be understood that the base 290 and head 292 are dimensioned so that the proximal end of the head stem section abuts the step within base 290 that defines the base of counterbore 304.

Adhesives hold the base 290 and head 292 together. The adhesives also create a seal around coil space 312. In some versions of the invention, base 290 and head 292 may be provided with tongue-and-slot members to further facilitate the mechanical connection of these components.

When hub 252 is seated in handpiece 250, coil 316 is aligned with the handpiece coil 260. Consequently, signals are inductively transmitted between the coils. In preferred versions of the invention, the voltage across the handpiece coil is approximately 5 to 25 volts, the current through the handpiece coil is approximately 25 to 125 mAmps. Given this strength of signal, and the fact that handpiece body 254 is metal, in preferred versions of the invention, the inductive field established by the handpiece coil does not extend more than 2 cm beyond the coil. In more preferred versions of the invention, this inductive field extends a maximum of 1 cm beyond the coil. Thus, the inductive field is sufficient to engage in signal transfer with the coil 316 of the hub inserted in the handpiece 250, but not the coil integral with a cutting accessory that may be located next to the handpiece.

It should likewise be understood that the system of this invention may have power-consuming devices other than motors. For example, in alternative versions of the invention, the handpiece power-consuming device may be some sort of heat generating device, light generating device or sound/mechanical-vibration generating device. The energy generated by these power-consuming devices are applied to surgical sites through removable accessories different from what has been described. The accessories of these versions of the system of this invention are provided with tags that have memories in which data describing the individual operating characteristics of the accessories are stored. Clearly, different data are contained in cutting accessories that are actuated by devices other than motors. Also, the chip may be installed in accessories that are not actuated. One such device is a pointer that is attached to a tracker that is used to facilitate the performance of surgical navigation.

It should likewise be understood that this invention may do more than simply provide data or write data to a cutting accessory attached to a handpiece. For example, some surgical tool systems include intermediate attachments 320, one shown diagrammatically in FIG. 20. These attachments 320 serve as mechanical, optical or electrical linkages between the power generating unit internal to the handpiece 22a and a cutting accessory 24a. In these versions of the invention, an RFID chip 322 is mounted in a non-metallic ring integral with the attachment (ring not illustrated). Upon connection of the attachment 320 to the handpiece, a coil 324 integral with the attachment is in close enough proximity to the handpiece coil 66a that there is an inductive signal transfer between these components. Based on the data read from the attachment, the control console 28 applies energization signals to the handpiece power generating unit so that it operates in a manner appropriate to the associated attachment and cutting accessories. For example, if the handpiece power generating unit is a motor, based on the data read from the attachment connected to the handpiece, the power generating unit can establish a maximum speed for the motor and/or determine the maximum torque the motor should be allowed to develop.

Figure 20:
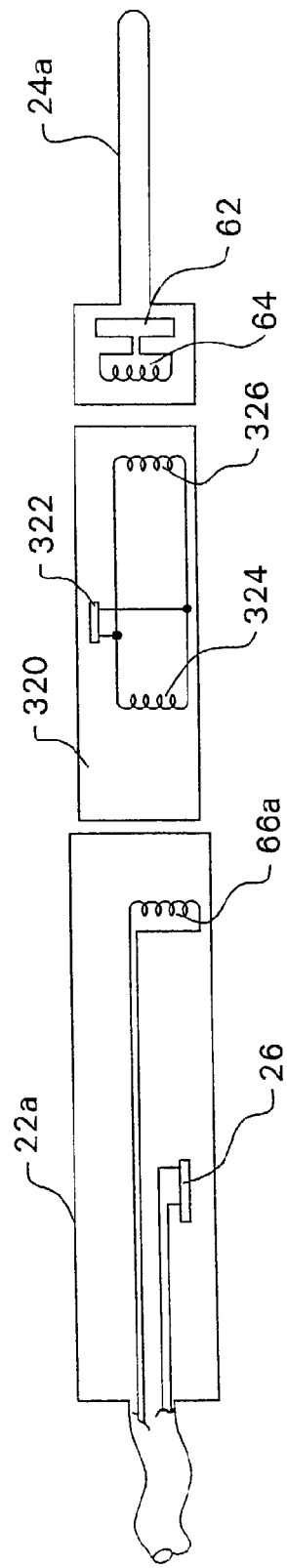
FIG. 20 is a block diagram view of an alternative version of this invention.

In the above versions of the invention, the attachment may, as depicted in FIG. 20, have its own coil 326 for inductive coupling to the RFID chip 62 integral with the associated cutting accessory 24a. In this version of the invention, the processor internal to the control console engages in the following data reading protocol. First, an interrogation signal is sent asking for data from an attachment RFID chip 322. Integral with this signal is data indicating the type of RFID chip, an attachment chip, that is supposed to respond to the interrogation. Based on these data, only the attachment chip 322 responds. After the data in the attachment RFID chip 322 are read, the control console generates a second interrogation signal. Embedded in this signal are data indicating that an accessory chip 62 is supposed to respond to the interrogation. Based on this interrogation signal, only the accessory RFID chip 62 writes out data back to the processor. Thus, the energizaton of the handpiece power generating unit is based on data in the attachment and/or any overriding data in the cutting accessory.

Figure 21:
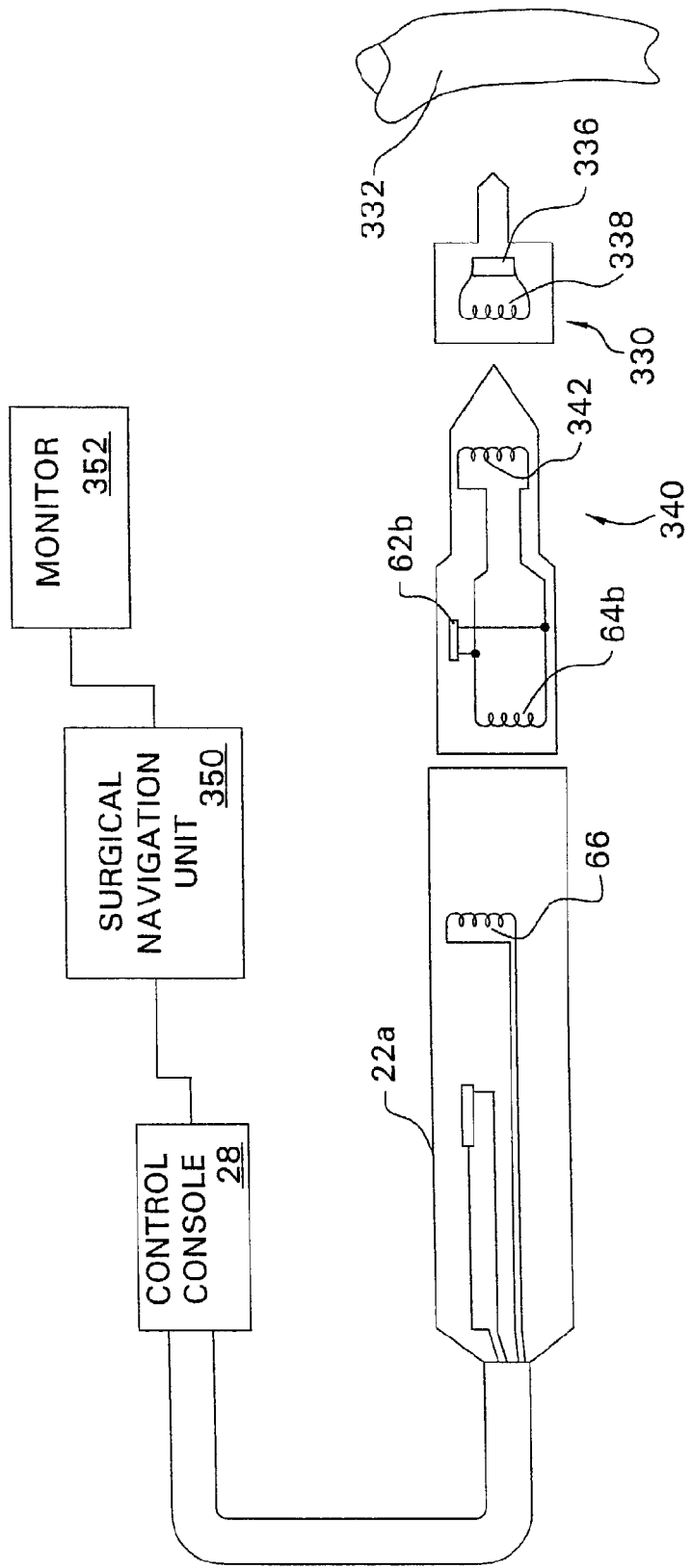
FIG. 21 is a block diagram depiction of how this invention may be integrated in a surgical navigation system.

Also, as depicted in FIG. 21, in some versions of the invention, an RFID chip may be placed in an implantable device 330 that is fitted into a patient, represented by bone section 332. Such devices include screws, reamers that are used to bore holes for implants, or implants themselves. Specifically the head of the device 330 is provided with a plastic ring in which an RFID chip 336 and complementary coil 338 are seated. The data in chip 336 include such information as the preferred and suggested maximum speeds for driving the implant into the patient. These data also describe the physical characteristics of the implant. For example, if the implant is a screw, the data describes: the implantable length of the screw; the diameter of the screw; and the size of the exposed head.

Figure 22:
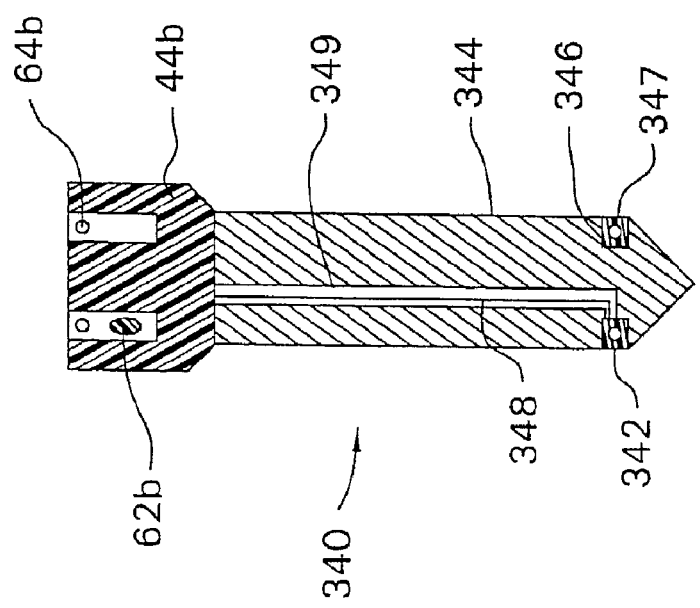
FIG. 22 is a cross sectional view of a cutting accessory of the version of this invention depicted in FIG. 21.

In this version of the invention, the accessory 340 used to set the implant, as seen in FIG. 22, is provided with a coil 342. Here, the accessory 340 is a screw driving shaft. The accessory has a shaft 344 formed of metal. Immediately proximal to the distal end, shaft 344 is formed to have a circumferentially extending groove 346. Coil 342 is disposed in a plastic or other non-metallic housing 347 seated in groove 346. Conductors, represented by a single conductor 348, extend through a conduit 349 that extends longitudinally through shaft 344. The conductors 348 are connected to a coil 64b disposed in the distal end hub 44b of the accessory 340. Distal end hub 44b, in addition to including coil 64b also includes an RFID chip 62b that contains data describing the characteristics of the accessory 340.

When the system of FIG. 21 is used, control console 28 is inductively coupled to both accessory chip 62b and implant chip 336. This coupling occurs immediately after the surgeon has depressed a control member associated with the system to actuate the handpiece 22b. This is because, at this time, the surgeon has typically already pressed the distal end head of the cutting accessory 340 against the adjacent head of the implant 330. Thus, at this time the data from the implant chip 336 can be read. The data in these chips are read by the control console 28. Based on these data, the control console regulates the application of energization signals to the handpiece 22b to ensure that the accessory 340 is driven at an appropriate speed for the complementary implant 330.

As part of this process, the control console 28 first verifies that the accessory 340 is an appropriate type of accessory for driving the implant. This verification may be performed by, first, determining the type of implant from the data read from the implant chip 336. Then, based on data contained in the memory internal to the control console 28, the control console determines if the accessory 340 can drive the implant. Alternatively, the data in the implant chip 336 contains a list of the types of accessories 340 that are appropriate for driving the implant. If initially, the control console 28, based on the determination of the type of accessory and the type of implant, determines that the accessory is inappropriate, the control console either provides a warning message that the surgeon must acknowledge this fact or prevents actuation of the handpiece 22b.

If the accessory 340 is an appropriate accessory for driving the implant, control console 28 configures the system so that energization signals are applied to the handpiece 22b that will cause the accessory to be driven at the preferred speed. If the surgeon attempts to drive the accessory above an appropriate maximum speed for the implant 330 or the accessory 340, at a minimum, the control console presents a warning the surgeon must acknowledge before the procedure is allowed to proceed.

Control console 28 also forwards the data regarding the characteristics of the implant 330 and the driving accessory 340 to a surgical navigation unit 350. Prior to this part of the procedure, the surgical navigation unit was provided with data that describes the physical dimensions of the portion of the patient on which the procedure is being performed. A tracker, not shown is attached to the handpiece 22b. The surgical navigation unit 350 monitors the position of the tracker. When the surgical procedure is being performed, the surgical navigation unit has the following data: position of the tracker; data regarding the physical characteristics of the handpiece 22a and accessory 340; and, from the implant chip 336, data regarding the physical characteristics of the implant 330. Based on these data and the stored image of the patient, the surgical navigation unit 350 is able to determine the position of the implant 330 as it is driven into the body of the patient 332. This information is presented on a monitor 352.

Also, the surgical navigation unit 350 determines, based on the stored data regarding the implant 330 and patient 332, if it appears that there is a possibility that the implant is being inappropriately positioned in the patient. For example, if the implant is a screw that is supposed to only be driven into bone to a certain depth, the surgical navigation unit monitors the extent to which the implant is driven into the bone. If it appears that continued driving of the implant into the bone is inappropriate, the surgical navigation unit 350 causes a warning to be presented. The surgical navigation unit 350 also inhibits the control console 28 for supplying energization signals to the handpiece 22b until the warning is acknowledged.

Figure 23:
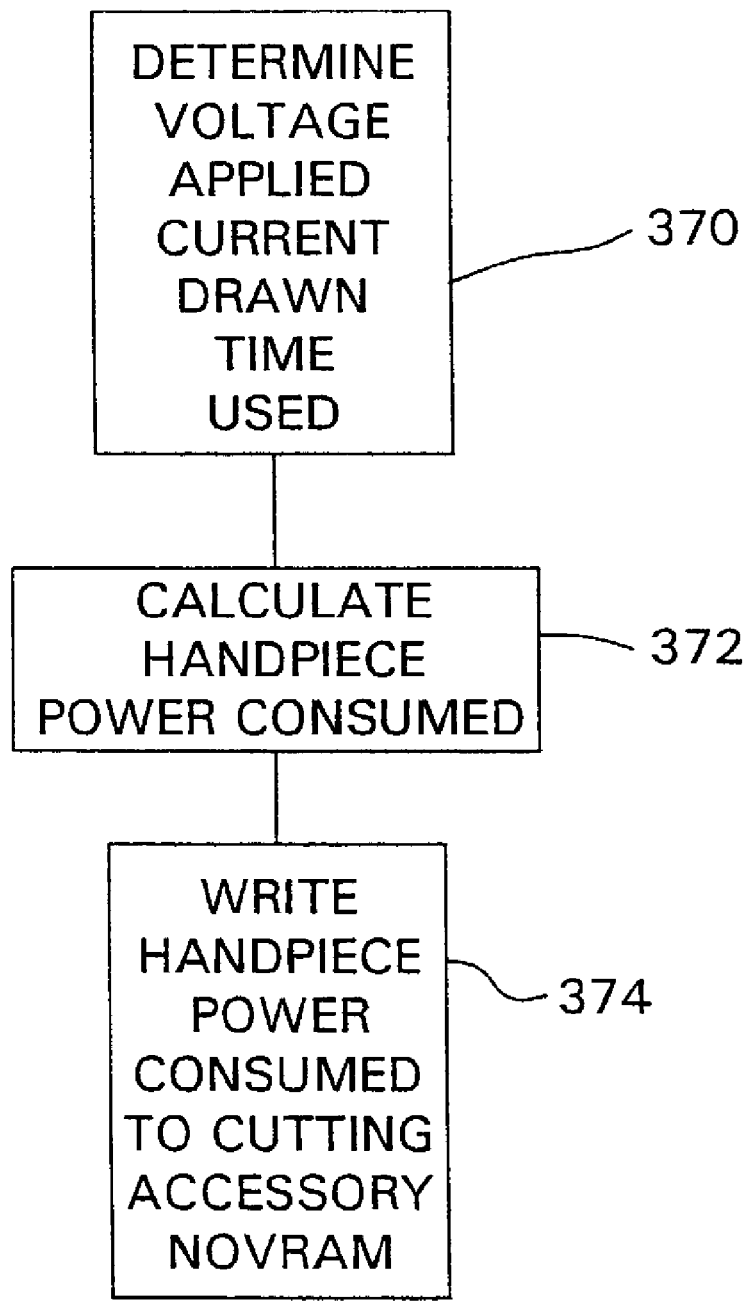
FIG. 23 is a flow chart depicting how the control console determines the extent to which a particular cutting accessory is worn.

Also, as mentioned above with respect to the data stored in chip controller/memory 84, this component may contain data that indicates the extent to which the cutting accessory is worn. One means of determining cutting accessory wear is now described by reference to FIG. 23. Specifically, controller 70, in addition to monitoring the amount of time a cutting accessory is actuated monitors the voltage applied to the handpiece that actuates the cutting accessory as well as the current drawn by the handpiece, step 370. When the handpiece motor is actuated, controller 70 performs step 372, a power consumed calculation for the handpiece. In step 372, based on the voltage applied to the handpiece, the current drawn and the time the handpiece was used, controller 70 determines the Watts minutes of power consumed by the handpiece.

Then, once the handpiece motor is turned off, in step 374, data representative of the power consumed by the handpiece is then written by the controller 70 into the WEAR PROFILE data field 112 of controller memory 84.

It should be understood that the data in the WEAR PROFILE data field 112 are used in the same generally manner as the data in the TIME USED field 110 are used. Specifically, these data are read by controller 70. During the use of the cutting accessory, in a location within the memory integral with control console 28 data representative of the cumulative watt minutes of power consumed in actuating the cutting accessory are stored. These data are based on the data read from the WEAR PROFILE field 112 as well as the data generated as a result of the periodic execution of steps 370 and 372 when the handpiece motor is actuated. These data representative of total cutting accessory wear are compared to a reference value. This reference value may be from data read from chip 62, (data storage field not shown) from the handpiece or a set value in the control console memory 69. If this comparison indicates that the total amount of power employed to drive the cutting accessory exceeds the reference value, a warning message is generated on the console display 71. This provides the surgeon with an indication that the cutting accessory may be worn to a level that the efficiency of the accessory has appreciably diminished.

Figure 24:
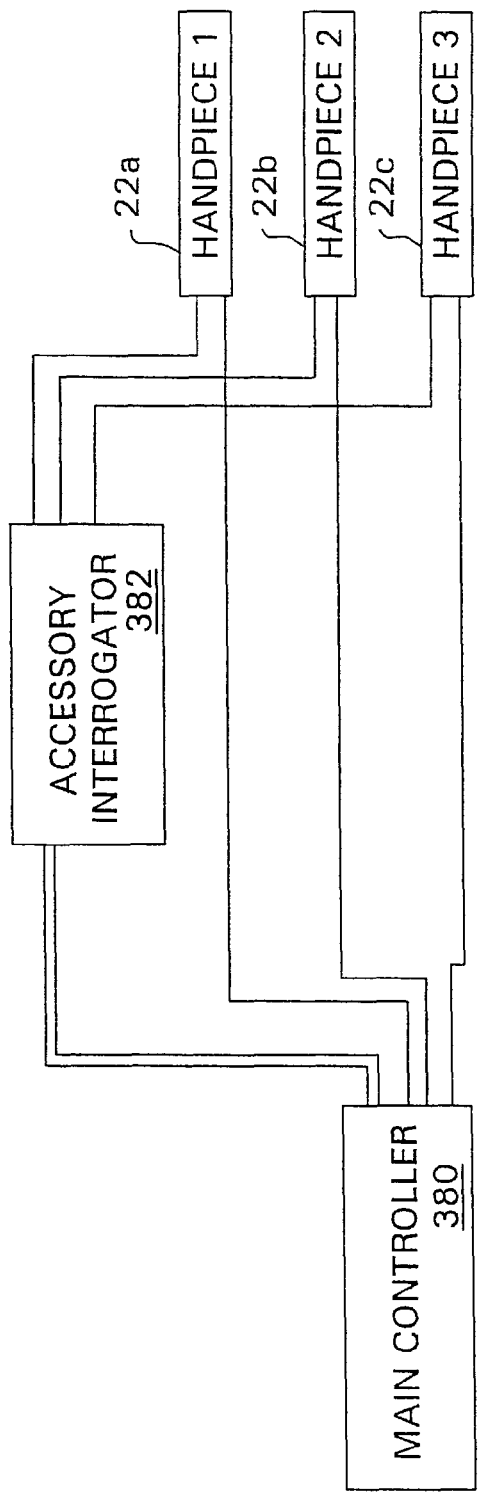
FIG. 24 is a block diagram of the inside of the control console depicting how separate controllers regulate the actuating of handpieces and the reading of data from the NOVRAMs integral with the cutting accessories attached to the handpieces.

FIG. 24 depicts in block diagram components internal to a control console to which plural handpieces may be simultaneously attached. Specifically, there is a first processor, main controller 380, and a second processor, accessory interrogator 382. The main controller 380 is the processor that has primary responsibility for generating the command signals to the drivers internal to the control console that supply the energization signals to the individual handpieces 22a, 22b and 22c, (drivers not shown). The input signals into main controller 380 include the characteristics of the individual handpieces as well as the surgeon-originating command signals that indicate the rate at which the handpieces are to be actuated.

The input signals into main controller 380 also include the data read from the identification chips 62 integral with the cutting accessories 24 attached to the individual handpiece 22a, 22b, and 22c. These data are retrieved by the accessory integrator 382. Once the accessory interrogator 382 retrieves these data, the interrogator forwards these data to the main controller 380. The main controller 380, in turn, generates command signals to the drivers to cause each handpiece 22a, 22b and 22c to be actuated appropriately for the attached cutting accessory 24.

Figure 25:
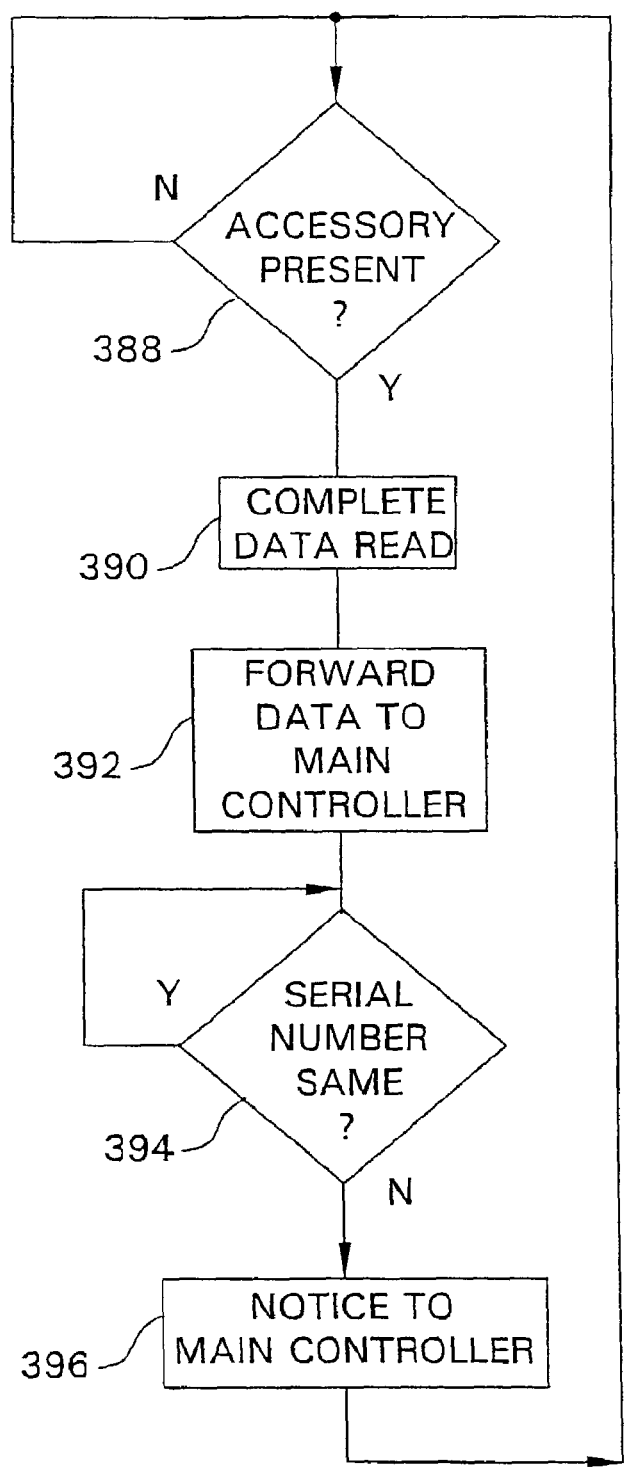
FIG. 25 is flow chart depicting an alternative process by which data in a cutting accessory NOVRAM are read.

FIG. 25 depicts one protocol for retrieving data from the cutting accessory identification chips. Specifically, after the main controller 380 determines that a handpiece 22a, 22b or 22c is connected to one of the control console 28 connections, the main controller instructs the accessory interrogator 382, to initiate an interrogation sequence for that handpiece, (step not shown). Initially, the interrogation sequence consists of accessory interrogator 382 generating a request that any attached accessory write back one specific type of data. This request, represented by step 388, is performed so that the accessory interrogator 382 can determine whether or not an accessory is even attached to the handpiece 22a, 22b or 22c. The accessory interrogator 382 performs this write request and waits for data step continually, as long as there is an attached handpiece. In one version of the invention, the specific data the accessory interrogator 382 requests is the cutting accessory serial number.

Upon attachment of a cutting accessory 24 to a handpiece 22a, 22b or 22c, the identification chip in the accessory will, in response to the write request, read out the serial number. Upon receipt of these data, accessory interrogator requests that all the data in the accessory identification chip 64 be written back. This write request and the subsequent data write out, are represented by step 390. In step 392 the identification chip data used to control operation of the cutting accessory 24 are forwarded to the main controller 380. The main controller, as discussed previously with regard to step 126, configures the system so that energization signals will be supplied to the handpiece 22a, 22b or 22c that will cause the appropriate energization of the attached cutting accessory 24.

After the data are read from the accessory identification chip 62, the accessory interrogator 382 continually generates a read request for the serial number of the accessory. This serial number is continuously compared to the serial number originally read for the cutting accessory. The read-request, data write and comparison steps collectively represented as step 394. These steps are performed in order to ensure that the same cutting accessory 24 remains attached to the handpiece 22a, 22b or 22c. As long as the same cutting accessory is attached to the particular handpiece, there is no change in the overall operation of the system.

If, however, the serial number is different, or no serial number is returned, the accessory interrogator 382 interprets the response indicating the accessory was removed or switched. Accessory interrogator 382 then proceeds to step 396. In step 396, the accessory interrogator generates a message to the main controller 380 informing the main controller of the disconnect of the cutting accessory. The main controller 380, in a step not shown, then regulates the energization of the associated handpiece as is appropriate for a cutting accessory not being attached. This particular regulation may, for example, consist of the inhibiting of the actuation of the handpiece.

The accessory interrogator 382 then reexecutes step 388. Step 388 is again repetitively reexecuted until it receives a serial number indicating a cutting accessory 24 has again been attached to the handpiece.

An advantage of the above arrangement is that, the majority of read requests generated by the accessory interrogator and subsequent data writes by the accessory NOVRAMs 32 are for relatively small amounts of data. This makes it possible for the accessory interrogator to, in a relatively short amount of time, monitor whether or not accessories 24 are attached to each of the handpieces 22a, 22b and 22c. Thus, in the event there is a removal or replacement of the cutting accessory attached to any one of the handpiece 22a, 22b or 22c, the accessory interrogator will detect this change, typically within 50 msec. or less of the event. Main controller 380 is then promptly informed of this state change so as to substantially eliminate the likelihood that a handpiece will be actuated even though there is no attached accessory, or actuated in an inappropriate manner for the attached handpiece.

Figure 26:
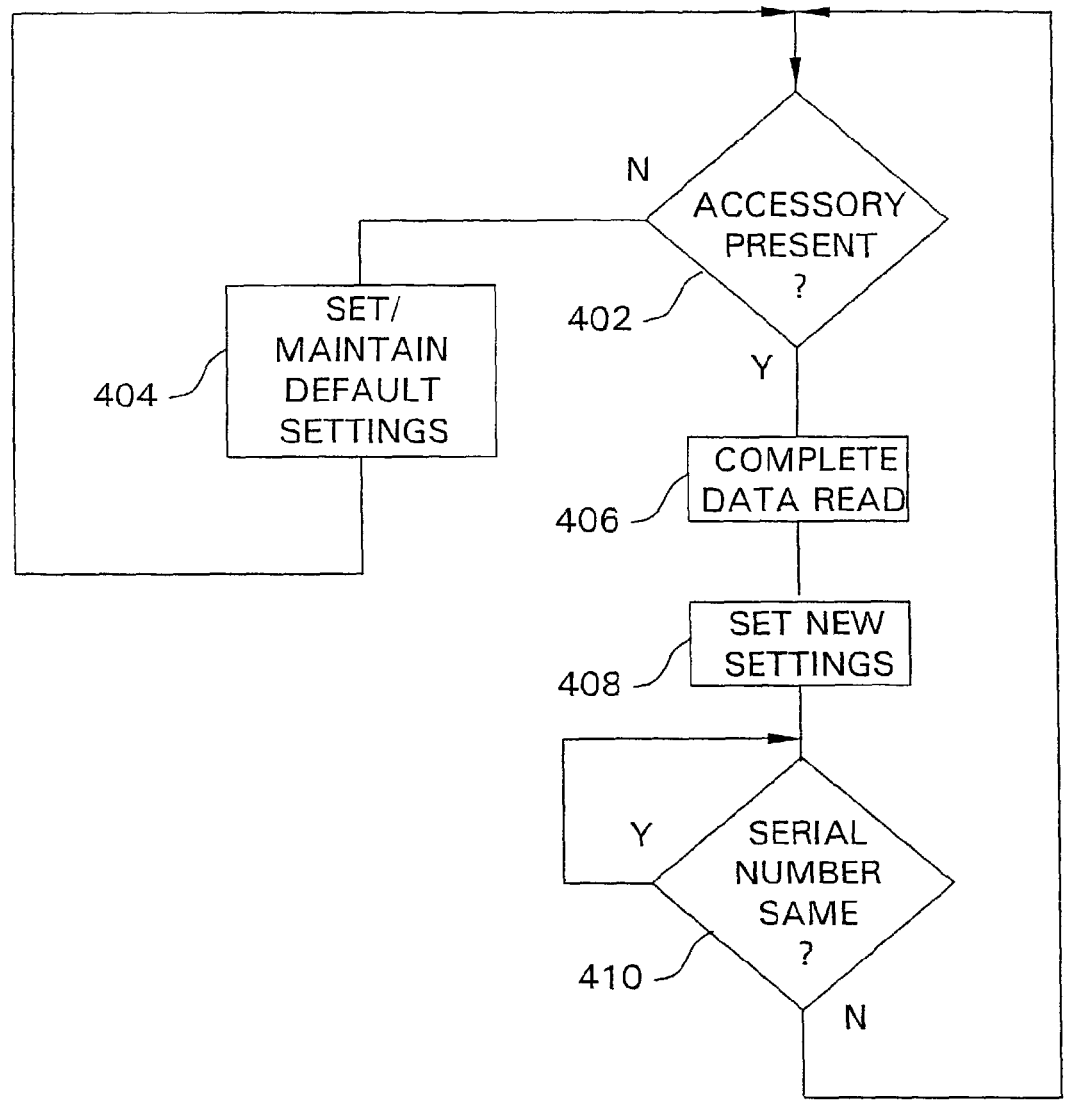
FIG. 26 is a flow chart depicting an alternative process by which data in a cutting accessory NOVRAM are read and the control console configured to energize the handpiece to which the cutting accessory is attached.

An alternative protocol for reading data from a cutting accessory identification chip 62 is now described by reference to FIG. 26. Here an accessory present read-request and receive written data step 402, identical to step 388, is performed as before whenever a handpiece 22a, 22b or 22c is connected to a control console 28. However, if the accessory interrogator 382 does not provide the main controller 380 with a data from accessory identification chip 62, in step 404, the main controller sets the control console to energize the handpiece 22a, 22b or 22c based on default setting for the handpiece. These settings are based on data in the handpiece NOVRAM. Accessory interrogator 382 and main controller 380 repetitively reexecute steps 402 and 404, respectively, until data are returned by an accessory identification chip 62.

Once data, again typically a serial number, are returned by the identification chip 62 of a newly installed cutting accessory 24, the accessory interrogator requests all the data in the chip, represented by step 406. These data are forwarded by the accessory interrogator 382 to the main controller 380, step not illustrated. Based on these data, in step 408, the main controller resets the data used to control the handpiece so that the handpiece 22a, 22b or 22c is energized appropriately for the attached cutting accessory 24. As before, even when the handpiece 22a, 22b or 22c is energized, the accessory interrogator 382 continues to request the serial number information from the accessory identification chip 62 to determine whether or not it has changed, step 410.

If, in step 410, it is determined that there has been a change in the cutting accessory 24 attached to the handpiece step 402 is again executed. Depending on the results of the inquiry performed in step 402 either step 404 or step 406 is again executed.

An advantage of this method of operation is that there may be some handpieces that are used primarily with one particular type of cutting accessory. The cutting accessory with which the handpiece is most often used is not provided with an identification chip. The handpiece NOVRAM 32 contains data setting the handpiece to operate in accordance with the characteristics of this particular cutting accessory. Thus, in this version of the invention, the cost of providing the most often used cutting accessory with an identification chip is eliminated.

Figure 27:
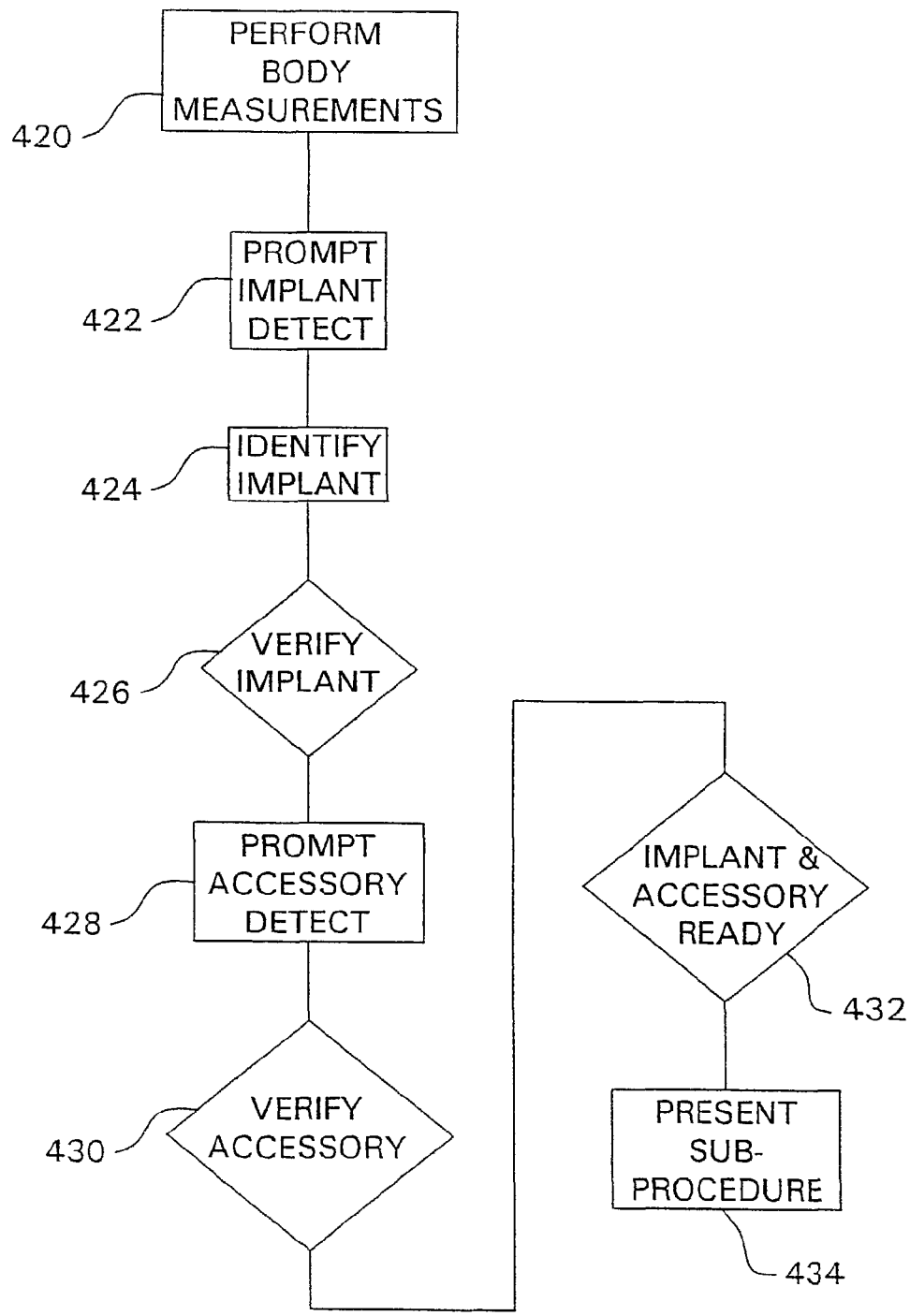
FIG. 27 is a flow chart depicting how the integrated cutting accessory and implant recognition system of this invention can be used to facilitate the performance of image guided surgery.

A more detailed explanation of how the cutting accessory and implant recognition system of this invention can be used in combination with a surgical navigation unit 350 is now described by reference to FIG. 27. Specifically, this invention can be used to facilitate the placement of an implant in a patient. As represented by step 420, initially the surgical navigation unit 350 is employed to measure the portion of the body of the patient to which the implant is to be fitted. Then, as represented by step 422, as part of the procedure, the surgical navigation unit generates a message prompting the surgeon to select an implant, or a particular component of an implant, for fitting to the patient.

The surgeon then identifies the implant 330, as represented by step 424. In this step, the surgeon identifies the specific implant by placing the handpiece 22 or cutting accessory 24 in close proximity to the implant so that the data in the implant chip 336 can be inductively written to the control console 28. In some versions of the invention, a passive surgical instrument, like a pointer with a built in coil, may be used to perform this data read-request and receive the written out data.

The data identifying the implant are written to the surgical navigation unit 350. The surgical navigation unit 350, in turn, based on input variables such as the dimensions of the implant and the measurements of the patient's body, determines whether or not the implant is appropriate for the procedure being performed, verify implant step 426. If, in step 426, the surgical navigation unit 350 determines that the implant might be inappropriate for the procedure, for example, the size appears inappropriate for the position in the body in which it is to be placed, the surgical navigation unit generates a warning to the surgeon, step not shown.

The next step in the procedure is the prompting by the surgical navigation unit 350 of the accessory that is to be used to fit the implant, step 428. The surgical navigation unit, in step 430, verifies that the accessory is the appropriate accessory for driving the implant. If an inappropriate accessory is selected, an appropriate warning is presented, warning step not shown.

In step 432 the surgical navigation unit 350 determines whether or not the accessory and implant are ready for the fitting of the implant. This step is performed by determine whether or not the signal transferred to the accessory coil 342 indicates the implant 330 is fitted to the accessory. Once the accessory and implant are ready for implant installation, the surgical navigation unit, in step 434, presents on monitor 352 information about the exact surgical sub procedure that is performed to fit the implant. This information may include an image of the site where the implant is to be fitted. This information may also include textual commentary regarding aspects of the procedure.

Thus, the integrated system of this invention provides guidance and prompts to the surgeon to facilitate the execution of the surgical procedure. This can minimize the time the patient is held under anesthesia which is one of the goals of modern surgery. Also, the implant and accessory verification steps serve to reduce the likelihood that an inadvertent oversight causes a surgeon to attempt to use a less than optimal component during a surgical procedure.

Figure 28:
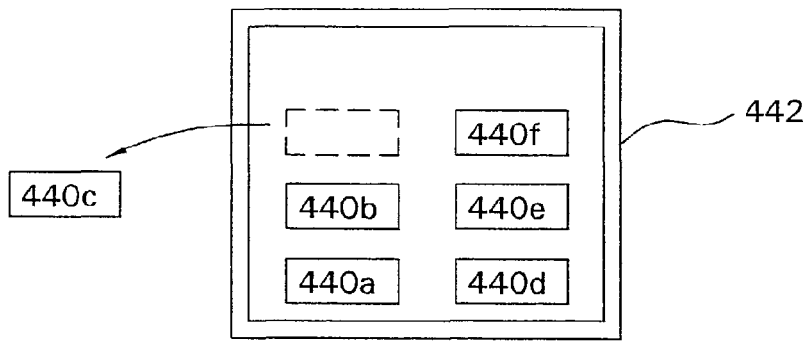
FIG. 28 is a diagrammatic illustration of a case, such as a sterilization case or a trial case, in which components used to facilitate the performance of a surgical procedure are held.

The cutting accessory and implant recognition system of this invention is also used to assist in the inventory of components used during a surgical procedure. As seen by reference to FIG. 28, components 440*a*, 440*b*, . . . 440*f* used to perform the procedure are kept in a case 442. For example, certain instruments may be held in a sterilization case. Alternatively trial implant components are held in a trial case.

As part of the procedure, the control console 28, in step 444, determines when a component is used. This determination occurs when an accessory is fitted to a handpiece or another device, for example an implant or an implant trial unit, is fitted in place with the handpiece or cutting accessory. As discussed above, the data in the chip integral with this instrument or implant is inductively read.

Figure 30:
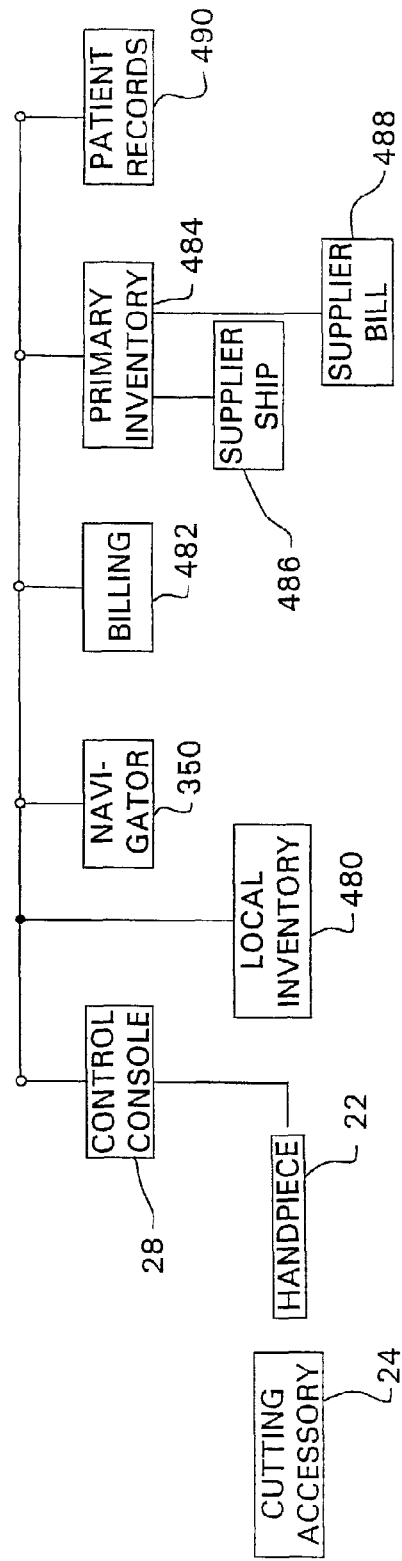
FIG. 30 is a block diagram of how the information generated by the integrated cutting accessory and implant recognition system of this invention are transferred to other components of a medical facility data information network.

As a consequence of this component used determination, a local inventory of used components is updated, step 446. A database in which these information is stored, a local inventory database 480, is connected to the control console as discussed below with respect to FIG. 30. Data are written to and read from this database 480 by a dedicated processor, not shown.

Figure 29:
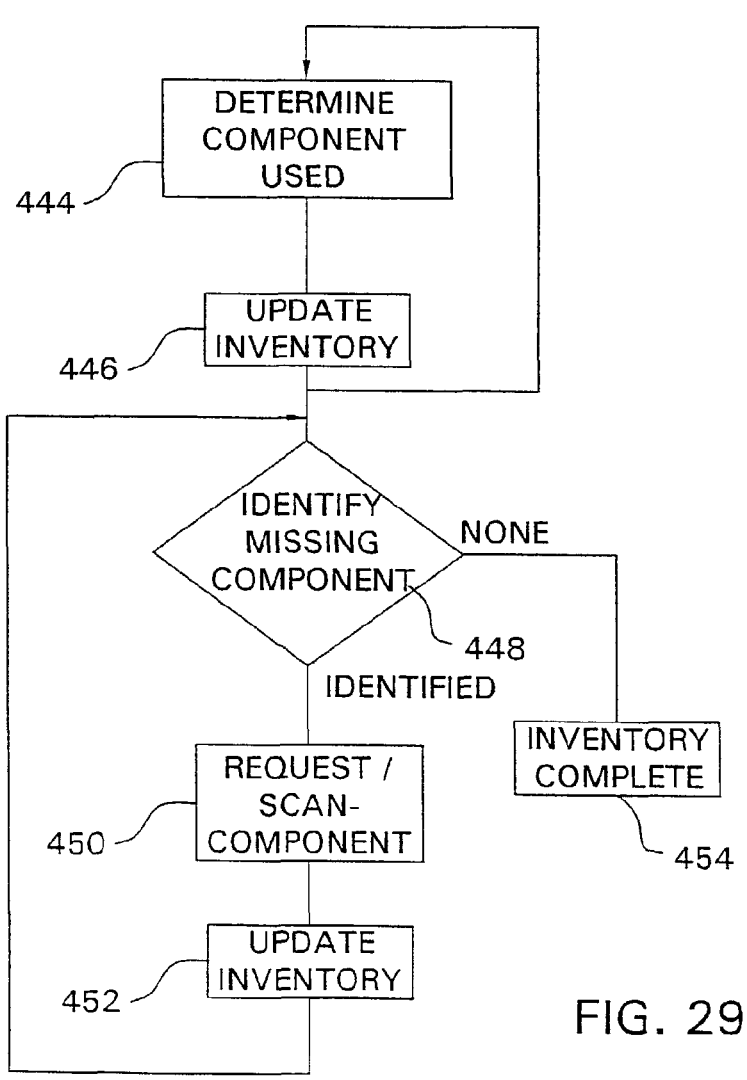
FIG. 29 is a flow chart depicting how the integrated cutting accessory and implant recognition system of this invention can be used to facilitate the inventory of components used during the performance of a surgical procedure.

Eventually, there is a point in the procedure in which it is time to inventory the used components to ensure that their whereabouts are known and they are properly stored. Typically this point is near the end of the procedure. At this time, the processor associated with the local inventory database 480 identifies a component that needs for which accounting is required, step 448. The identity of this component is sent to either the control console 28 or the surgical navigation unit 350. The device that receives this information, in step 450, requests the surgical personnel to locate this component. In response to this request, also part of step 450 in FIG. 29, the personnel return the component 440*a*, 440*b*. . . or 440*f* to the case 442 in which the component is stored and inductively read the stored identifying information for the component.

Data indicating that the component has been properly returned to the case 442 are forwarded to the processor associated with the local inventory database 480. This processor, in step 452, updates the inventory for the particular case 442. The local inventory database processor then reexecutes step 448. If there are still missing components, step 450 is reexecuted and one of the remaining missing components is again identified. However, in step 448 it may be determined that all the components are accounted for. If the local inventory database processor makes this determination, this processor causes the control console 28 or navigation unit 350 to display a message indicating that the inventory is complete, step 454.

The above aspect of this invention facilitates the checking of equipment used during surgery to ensure the whereabouts of this equipment is known.

As mentioned above, and now described by reference to FIG. 30, the information generated by the accessory and implant recognition system of this invention may be employed by components other than the control console that drive the handpieces used to actuate the accessories. Specifically, as seen in this Figure, the control console that reads the accessory and implant identify data may be attached to a local area network to which other equipment both in the operating room and elsewhere in the medical facility are attached. In one version of a network it is contemplated that this data transfer be over a serial bus in accordance with the IEEE-1394 data transfer protocol.

Three devices attached this network are the control console 28, the surgical navigation unit 350 and the local inventory database 480.

The facility's billing processor, represented by node 482 is also attached to this network. The billing processor receives data packets identifying the patient-chargeable components identified by the control console that are used during the procedure. This facilitates the accurate charging of the patient for the equipment used during the surgical procedure.

The records of components used are also forwarded to facility's primary inventory control database, node 484. This allows the processor that monitors inventory levels of the accessories and implants to determine when the additional equipment needs to be shipped, represented by supplier ship node 486. Also, some suppliers only bill the facility when the equipment is actually used. The inventory control database, upon receiving an indication that some equipment has been used, through a supplier bill node 488 informs the supplier's processor of this event. This arrangement thus makes it possible to ensure that a facility is only billed for equipment when the equipment is used.

Also the database in the facility that maintains patient records, represented by node 490, receives an indication of the cutting accessories, trial components, and implants fitted during the surgical procedure. Thus, medical personnel do not, during the procedure have to spend time documenting what specific components where used during the procedure. Since the use of these components can readily be data stamped, the personnel likewise do not have to document when these components were used.

Also, there is no reason that in all versions of the invention the tags be inductively coupled to the complementary handpieces in which their accessories are inserted. In some versions of the invention, there may be physical connections between the exposed contacts that are part of the handpiece and accessory. These contacts, upon physical abutment, establish the connection between the accessory tag and the conductors in the handpiece that extend to the control console.

Furthermore, in some versions of the invention, the coil that inductively couples the signal to the cutting accessory may not be in the handpiece. In some versions of the invention, this coil may be located in the control console. Whenever a new cutting accessory is attached to the handpiece, information about this event is sensed by a device internal to the handpiece and a signal representative of this event is forwarded to the control console. The control console then generates a message directing the surgeon to place the handpiece and cutting accessory sub-assembly adjacent a particular location on the control console to facilitate the inductive transfer of signals between the console and the accessory tag. An advantage of this version of the invention is that it eliminates the need to provide additional conductors in the cable that extends to the handpiece.

Figure 31:
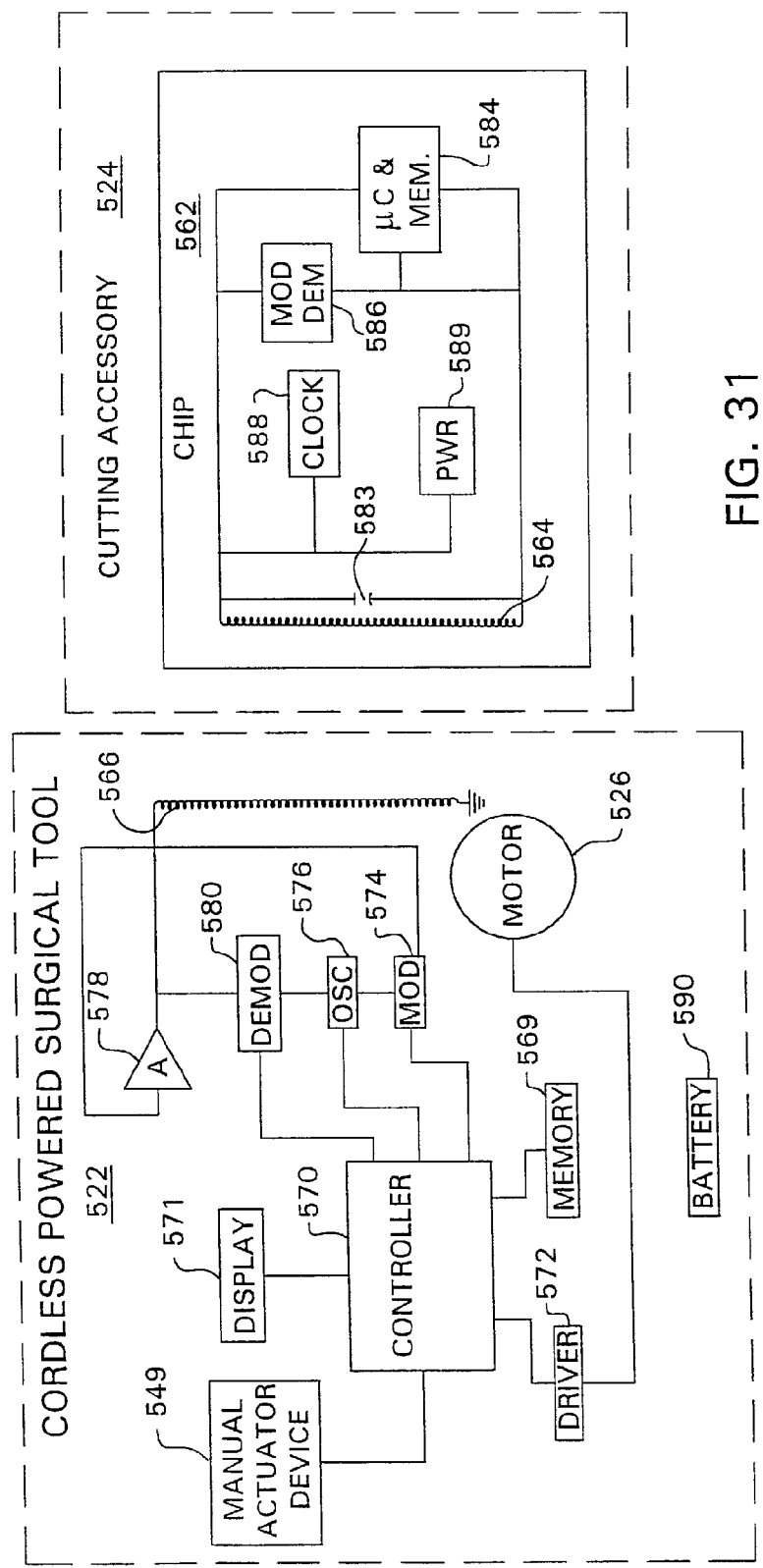
FIG. 31 is a block diagram of the circuitry internal to a cordless powered surgical tool and a cutting accessory that is used therewith.

Another embodiment of the invention is shown in FIG. 31. In this embodiment, no cable connects the handpiece or cordless powered surgical tool to a control console. The Applicant's Assignee's U.S. patent application, CORDLESS, POWERED SURGICAL TOOL Ser. No. 10/210,325, filed on Aug. 1, 2002, now U.S. Pat. No. 6,960,894 B2, and incorporated herein by reference, provides details of a physical structure of a cordless powered surgical tool. Likewise Applicant's Assignee's U.S. Pat. No. 5,747,953 entitled CORDLESS, BATTERY OPERATED SURGICAL TOOL, issued May 5, 1998, and incorporated herein by reference, describes a surgical tool that may be modified to include the circuit arrangement shown in FIG. 31.

As shown in FIG. 31, the cutting or operating end of the cordless surgical tool 522 is provided with an annular coil 566. Collectively, the cordless surgical tool 522 and cutting accessory 524 are shaped so that coils 564 and 566 are in such proximity to each other that they will collectively inductively transfer signals from/to the circuit internal to the surgical tool 522 to/from the circuit internal to the identification chip 562. Typically, the housing of the surgical tool 522 is formed of materials discussed in Applicant's above patent documents.

The surgical tool 522 includes a battery 590 that supplies power, as necessary, to the circuit elements therein (connections not shown). A controller 570 controls the overall operation of the system. Memory 569 in the surgical tool 522 contains the permanent operating instructions that are executed by controller 570 to control the system and regulate the actuation of the surgical tool 522 and the cutting accessory 524. Controller 570 generates energization control signals to a driver 572. The energization control signals are based on the cutting accessory 524 identified and the value selected by a manual actuator device 549. The manual actuator device 549 can be a trigger type push button controlling the output from a variable resistor or any other type of device providing a variable signal output. The driver 572, based on the value of the output from the manual actuator device 549 and the cutting accessory 524 identified, generates the energization signals that are applied to the surgical tool motor 526.

The surgical tool 522 can also include a touch screen display 571 or other type of indicator/input system. Controller 570 causes information regarding the state of the system to be presented on the display 571. Controller 570 can also cause images of buttons to be presented on the display 571. An operator regulates the operation of the system by selectively depressing these buttons. In other embodiments, no indicator or display is present. The system automatically controls the cutting accessory 524 based on the accessory identified. For example, the maximum operating speed of the cutting accessory 524 can be varied depending of the accessory identified.

The surgical tool 522 also includes a modulator (MOD) 574 that modulates digital signals output by controller 570 so they can be inductively transferred to cutting accessory identification chip 562. In one preferred version of the invention, modulator 574 receives a fixed-frequency signal from an oscillator 576 internal to the surgical tool 522.

Modulator 574 produces an amplitude shift keyed signal generated by modulator 574 that is amplified by an amplifier 578. The output signal from amplifier 578 is applied to one end of coil 566.

Demodulator 580 receives a signal that is coupled to coil 566, demodulates the signal, and applies the output bit stream to controller 570.

The identification chip 562 can include a small controller and an electronically programmable memory (μC & MEM) 584. The controller integral with controller/memory 584 controls the writing of data into its complementary memory section and the reading out of the contents of the memory. Modulator/demodulator (MOD DEM) 586, clock 588, capacitor 583 and power regulator 589 function in substantially the same manner as described for the embodiment in FIG. 3.

In FIG. 31, coil 564 is shown as being integrally part of chip 562. This is one option for the invention. However, as discussed above, it is anticipated that in many versions of the invention, chip 62 and coil 564 will be separate components.

Some of the different types of data stored in the tag controller/memory 584 include a serial number specific to the cutting accessory 524 with which tag 562 is integral. This number may also include a special authorization code. There is also stored data that indicates the type of cutting accessory 524. For example, the cutting accessory 524 may be a drill, saw, burr, linkage assembly for converting rotary movement to a back-and-forth movement, or other types of elements. In cases where a linkage assembly is utilized, an identification tag may be provided on the linkage assembly as well as a cutting element secured to the linkage assembly. The linkage assembly can function as an intermediate attachment between the surgical tool 522 and the cutting accessory 524 in a manner similar to the arrangement shown in FIG. 20.

The stored data can include the size, diameter, physical materials, and type of cutting accessory 524. The data can also include the preferred operating speed, maximum operating speed, maximum operating torque, stopping torque, or other type of information regarding operation of the cutting accessory 524. The mode of operation of the cutting accessory 524, such as oscillatory or unidirectional can also be provided with the data.

Data indicating if and when the cutting accessory 524 was previously used, and for how long can be read and written to the chip 562. Data indicating how long a surgeon can expect to use the cutting accessory 524 before the cutting/drilling surfaces become worn to the level at which they may not efficiently cut tissue can be read/stored.

The cordless surgical tool 522 of FIG. 31 operates in a similar manner to the handpieces connected by cables 30 in embodiments discussed above.

In another embodiment, the accessory 524 comprises an implant device, such as a screw or other element that is directly implanted into the body of a patient using the surgical tool 522. In this instance, the characteristics of the accessory element are provided to the surgical tool 522 regarding desired torque, operating speed, etc. for implanting the implant device.

Therefore, it is an object of the appended claims to cover all such variations and modifications that come within the true spirit and scope of this invention.

What is claimed is:

1. A powered surgical handpiece, said handpiece having:
    a housing, said housing having a first bore with an open end for removably receiving a cutting accessory and that extends inwardly into said housing;
    a motor disposed in said housing, said motor including a coupling assembly disposed in the housing first bore for engaging the cutting accessory so that, upon actuation of said motor, the cutting accessory is driven by said motor;
    a locking assembly mounted to said housing, said locking assembly having a member that engages said cutting accessory so as to removably hold said cutting accessory in the housing first bore; and
    a flexible carrier, said flexible carrier having first and second sections, each section having a longitudinal axis wherein: the longitudinal axis of the second section is angularly offset from the longitudinal axis of the first section; conductive traces are formed on the sections and are connected to each other; the carrier first section is wound in a closed circular pattern and disposed in a portion of said housing the defines the housing first bore so that the conductive trace on the carrier first section forms a coil that extends circumferentially around said housing first bore that is capable of inductively exchanging signals with the cutting accessory; and the carrier second section extends proximally from the carrier first section through said housing so that the conductive trace on the carrier second section functions as a conductor internal to said housing that extends to said coil.

2. The surgical handpiece of claim 1, wherein said locking assembly member is moveably attached to said housing.

3. The surgical handpiece of claim 1, wherein said housing is further formed to define a second bore that extends from the first bore to a location spaced from the first bore opening through which a suction is drawn.

4. The surgical handpiece of claim 1, wherein:
    said housing is formed with a second bore separate from said first bore that is connected to the first bore; and
    the second section of said flexible carrier is disposed in the housing second bore.

5. The surgical handpiece of claim 1, wherein an impedance matching circuit is attached to the second section of said flexible carrier and is connected to said coil formed by the conductive trace on the first section of said flexible carrier.

6. The surgical handpiece of claim 1, wherein:
    internal to said housing is an annularly shaped structural member having an inner surface that at least partially defines the housing first bore, said annularly shaped structural member being further shaped to define a groove that extends around and is separated from the housing first bore; and
    the first section of said flexible carrier is disposed in the groove defined by the annularly shaped structural member.

7. A powered surgical handpiece, said handpiece comprising:
    a body having a distal end, said body having a first bore that is open at the body distal end, the first bore dimensioned for removably receiving a cutting accessory;
    an annularly shaped structural member disposed in said body adjacent the distal end, said structural member shaped to have an inner wall that at least partially defines the body first bore and that defines a groove that extends annularly around the body first bore and that is isolated from the body first bore;
    a motor disposed in said housing, said motor including a coupling assembly disposed in the body first bore for engaging the cutting accessory so that, upon actuation of said motor, the cutting accessory is driven by said motor;
    a locking assembly mounted to said body, said locking assembly having a member that engages said cutting accessory so as to removably hold said cutting accessory in the body first bore;
    a flexible carrier, said flexible carrier having formed thereon at least one conductive trace wherein: said carrier has a first section with a longitudinal axis and a second section that is contiguous with the first section and that has a longitudinal axis that extends angularly away from the longitudinal axis of the first section; the first section of said flexible carrier, including said conductive trace on the first section, is wound in a closed circular pattern and disposed in the groove defined by said annularly shaped structural member so that the conductive trace on the carrier first section forms a coil that extends circumferentially around said housing first bore that is capable of inductively exchanging signals with the cutting accessory; and the carrier second section extends proximally away from the groove so that the conductive trace on the carrier second section functions as a conductor that extends to said coil.

8. The surgical handpiece of claim 7, wherein said body is further formed to define a second bore that extends from the first bore at a location spaced from the first bore opening through which a suction is drawn.

9. The surgical handpiece of claim 7, wherein:
    said body is formed with a second bore separate from said first bore that is connected to the first bore; and
    the second section of said flexible carrier is disposed in the second bore of said body.

10. The surgical handpiece of claim 7, wherein an impedance matching circuit is attached to the second section of said flexible carrier and connected to the coil-forming conductive trace on the first section of said carrier.

11. The surgical handpiece of claim 7, wherein said annularly shaped structural is member is shaped so that the groove defined by said structural member extends inwardly from and circumferentially around an outer surface of said structural member.

12. The surgical handpiece of claim 7, wherein the flexible carrier first section overlaps the flexible carrier second section and a conductive connection extends from the conductive trace on the flexible carrier first section to the conductive trace on the flexible carrier second section.

13. The surgical handpiece of claim 7, wherein the first and second sections of said flexible carrier are collectively L-shaped.

14. A powered surgical handpiece, said handpiece having:
   a body, said body having a first bore with an open end for removably receiving a cutting accessory and that extends inwardly into said body:
   a motor disposed in said housing, said motor including a coupling assembly disposed in the body first bore for engaging the cutting accessory so that, upon actuation of said motor, the cutting accessory is driven by said motor;
   a locking assembly mounted to said body, said locking assembly having a member that engages said cutting accessory so as to removably hold said cutting accessory in the body first bore;
   a flexible circuit, said flexible circuit having formed thereon at least one conductive trace wherein: said flexible circuit is formed to have first and second sections such that the flexible circuit first and second sections have longitudinal axes that are angularly offset from each other; the first section of said flexible circuit, including the conductive trace on the first section, is wound in a closed circular pattern and disposed in a portion of said housing the defines the body first bore so that the conductive trace wound in a circular pattern forms a coil that extends circumferentially around said housing first bore capable of inductively exchanging signals with the cutting accessory; and the second section extends proximally away from the first section so that the conductive trace of the flexible circuit second section functions as a conductor that extends to said coil; and
   an impedance matching circuit mounted to the second section of said flexible circuit, said impedance matching circuit being connected to said at least one conductive trace to function as an impedance matching circuit for said coil.

15. The surgical handpiece of claim 14, wherein said body is further formed to define a second bore that extends from the first bore at a location spaced from the first bore opening through which a suction is drawn.

16. The surgical handpiece of claim 14, wherein:
   said body is formed with a second bore separate from said first bore that is connected to the first bore; and
   the second section of said flexible circuit is disposed in said the housing body second bore.

17. The surgical handpiece of claim 14, wherein:
   an annular member is disposed in said body, said annular member having an inner wall that at least partially defines the body first bore and defining a groove that extends circumferentially around the body first bore that is isolated from the body first bore; and
   the first section of said flexible circuit is disposed in the groove defined by said annular member.

18. The surgical handpiece of claim 17, wherein said annular member is separate component from said body.

19. The surgical handpiece of claim 14, wherein: the flexible circuit first section is wound over a portion of the flexible circuit second section; and
   where the flexible circuit first section overlaps the flexible circuit second section, a conductive connection extends from said conductive trace on the flexible circuit first section to the conductive trace on the flexible circuit second section.

20. The surgical handpiece of claim 14, wherein the first and second sections of said flexible circuit are collectively L-shaped.

* * * * *